(12) United States Patent
Jeon et al.

(10) Patent No.: US 11,800,796 B2
(45) Date of Patent: Oct. 24, 2023

(54) LUMINESCENT MATERIAL FOR DELAYED FLUORESCENCE AND ORGANIC ELECTROLUMINESCENT DEVICE COMPRISING THE SAME

(71) Applicant: Rohm and Haas Electronic Materials Korea Ltd., Cheonan (KR)

(72) Inventors: Jeong-Hwan Jeon, Gwangju-si (KR); Hong Yeop Na, Hwaseong (KR); Hee-Choon Ahn, Seoul (KR)

(73) Assignee: Rohm and Haas Electronic Materials Korea Ltd.

( * ) Notice: Subject to any disclaimer, the term of this patent is extended or adjusted under 35 U.S.C. 154(b) by 189 days.

(21) Appl. No.: 15/738,335

(22) PCT Filed: Jul. 20, 2016

(86) PCT No.: PCT/KR2016/007885
§ 371 (c)(1),
(2) Date: Dec. 20, 2017

(87) PCT Pub. No.: WO2017/014546
PCT Pub. Date: Jan. 26, 2017

(65) Prior Publication Data
US 2018/0190912 A1    Jul. 5, 2018

(30) Foreign Application Priority Data

Jul. 20, 2015  (KR) .................. 10-2015-0102268
Jul. 8, 2016  (KR) .................. 10-2016-0086820

(51) Int. Cl.
| | | |
|---|---|---|
| *H10K 85/60* | (2023.01) | |
| *C09K 11/06* | (2006.01) | |
| *C07D 491/147* | (2006.01) | |
| *C07D 403/04* | (2006.01) | |
| *C07D 487/04* | (2006.01) | |
| *C07D 401/14* | (2006.01) | |
| *C07D 413/04* | (2006.01) | |
| *C07D 413/14* | (2006.01) | |
| *C07D 401/04* | (2006.01) | |
| *C07D 471/04* | (2006.01) | |
| *C07D 405/04* | (2006.01) | |
| *C07D 409/14* | (2006.01) | |
| *C07D 403/14* | (2006.01) | |
| *H10K 50/11* | (2023.01) | |
| *C07D 405/14* | (2006.01) | |

(52) U.S. Cl.
CPC ....... *H10K 85/6572* (2023.02); *C07D 401/04* (2013.01); *C07D 401/14* (2013.01); *C07D 403/04* (2013.01); *C07D 403/14* (2013.01); *C07D 405/14* (2013.01); *C07D 409/14* (2013.01); *C07D 413/04* (2013.01); *C07D 413/14* (2013.01); *C07D 471/04* (2013.01); *C07D 487/04* (2013.01); *C07D 491/147* (2013.01); *C09K 11/06* (2013.01); *H10K 85/654* (2023.02); *H10K 85/657* (2023.02); *H10K 85/6574* (2023.02); *H10K 85/6576* (2023.02); *C09K 2211/1018* (2013.01); *H10K 50/11* (2023.02); *H10K 85/636* (2023.02)

(58) Field of Classification Search
CPC .. C07D 401/04; C07D 401/14; C07D 403/04; C07D 403/14; C07D 405/14; C07D 409/14; C07D 413/04; C07D 413/14; C07D 471/04; C07D 487/04; C07D 491/147; C07D 209/82; C09K 11/06; C09K 2211/1018; C09K 209/82; C09K 2211/1029; C09K 2211/1044; H01L 51/0061; H01L 51/0067; H01L 51/0071; H01L 51/0072; H01L 51/0073; H01L 51/0074; H01L 51/5012; H10K 85/6572; H10K 85/654; H10K 85/657; H10K 85/6574; H10K 85/6576; H10K 50/11; H10K 85/636; H10K 2101/20
See application file for complete search history.

(56) References Cited

U.S. PATENT DOCUMENTS

| | | | |
|---|---|---|---|
| 10,227,528 B2 * | 3/2019 | Jatsch | C07D 401/04 |
| 10,249,828 B2 * | 4/2019 | Stoessel | C09K 11/06 |
| 2012/0241732 A1 | 9/2012 | Endo et al. | |
| 2013/0248849 A1 * | 9/2013 | Feldman | H05B 33/14 257/40 |
| 2014/0131665 A1 | 5/2014 | Xia et al. | |
| 2014/0138627 A1 | 5/2014 | Kwong et al. | |

(Continued)

FOREIGN PATENT DOCUMENTS

| | | |
|---|---|---|
| WO | 2015037965 A1 | 3/2015 |
| WO | 2015/093814 A1 | 6/2015 |

(Continued)

OTHER PUBLICATIONS

Dyes and Pigments 83 (2009), pp. 269-275. (Year: 2009).*

(Continued)

*Primary Examiner* — Dawn L Garrett

(74) *Attorney, Agent, or Firm* — G. Creston Campbell

(57) ABSTRACT

The present invention relates to a luminescent material for delayed fluorescence and an organic electroluminescent device comprising the same. By using the luminescent material for delayed fluorescence according to the present invention, an organic electroluminescent device having long lifespan, low driving voltage, excellent color purity, and significantly improved luminous efficiency such as current efficiency is provided.

6 Claims, 4 Drawing Sheets

(56) References Cited

U.S. PATENT DOCUMENTS

| | | |
|---|---|---|
| 2015/0041784 A1 | 2/2015 | Shizu et al. |
| 2015/0053938 A1* | 2/2015 | Zeng .................. H01L 51/0054 438/46 |
| 2015/0318478 A1* | 11/2015 | Pflumm .................. C09B 19/00 252/500 |
| 2015/0333274 A1* | 11/2015 | Parham ................ C07D 405/14 257/40 |
| 2016/0006959 A1 | 1/2016 | Machida |
| 2016/0181545 A1* | 6/2016 | Stoessel ............. H01L 51/0004 257/40 |
| 2016/0197286 A1 | 7/2016 | Kawamura et al. |
| 2017/0117485 A1 | 4/2017 | Cho et al. |
| 2017/0141326 A1 | 5/2017 | Kang et al. |
| 2017/0148998 A1 | 5/2017 | Kang et al. |
| 2017/0301867 A1 | 10/2017 | Kim et al. |
| 2017/0346022 A1* | 11/2017 | Ma ...................... H01L 27/3213 |
| 2018/0006237 A1* | 1/2018 | Anemain ............. C07D 495/04 |

FOREIGN PATENT DOCUMENTS

| | | |
|---|---|---|
| WO | 2015/093878 A1 | 6/2015 |
| WO | 2015084021 A1 | 6/2015 |
| WO | 2015/099507 A1 | 7/2015 |
| WO | WO 2015/182994 A1 * | 12/2015 |

OTHER PUBLICATIONS

Tetrahedron Letters 52 (2011), pp. 6942-6947. (Year: 2011).*
Shizu et al., Journal of Physical Chemistry C, (2015), vol. 119, pp. 1291-1297. (Year: 2015).*
Thomas, K. J., Lin, J. T., Tao, Y. T., & Chuen, C. H. (2002). Green and yellow electroluminescent dipolar carbazole derivatives: Features and benefits of electron-withdrawing segments. Chemistry of materials, 14(9), 3852-3859. (Year: 2002).*
Yang, Zhiyong, et al. "Recent advances in organic thermally activated delayed fluorescence materials." Chemical Society Reviews 46.3 (2017): 915-1016. (Year: 2017).*

* cited by examiner

LUMINESCENT MATERIAL FOR DELAYED FLUORESCENCE AND ORGANIC ELECTROLUMINESCENT DEVICE COMPRISING THE SAME

TECHNICAL FIELD

The present invention relates to a luminescent material for delayed fluorescence and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

Generally, an organic electroluminescent device (OLED) has a structure comprising a cathode, an anode, and an organic layer between them. When a voltage is applied, holes are injected from the anode, and electrons are injected from the cathode. Holes and electrons are recombined at a light-emitting layer to form an exciton of high energy. Due to the energy of the exciton, the organic luminescent material transfers to an excited state, and emits light when it returns to a ground state.

An organic light-emitting material can be used as a combination of a host and a dopant to improve color purity, luminous efficiency, and stability. Generally, an EL device having excellent luminous characteristics has a structure comprising a light-emitting layer formed by doping a dopant to a host. Since host and dopant materials greatly influence the efficiency and lifespan of the EL device when using a dopant/host material system, their selection is important.

Due to a spin rule based on quantum mechanics, singlet excitons and triplet excitons are formed at a rate of 25%: 75% in an organic electroluminescent device. Making use of singlet excitons is a fluorescent dopant. Theoretically, a fluorescent dopant is known to have a limit of 25% for an internal quantum efficiency of an organic electroluminescent device. On the contrary, since a phosphorescent dopant based on a metal complex using Ir, etc., emits light by making use of triplet excitons, the internal quantum efficiency can be up to 100%. However, the metal complex such as Ir has a high price and limited reserves. Thus, development of an alternative dopant is urgent.

Accordingly, a luminous material using delayed fluorescence is being developed recently as a luminous material of high efficiency, of which the internal quantum efficiency can exceed 25%, i.e. the limited efficiency of a fluorescent dopant material without using a metal complex as in a phosphorescent dopant material.

Normally, light-emission is completed within a short time of 100 ns or shorter in fluorescence. A fluorescence which continues to emit light for a much longer time of μs units or longer is called delayed fluorescence. Delayed fluorescence is classified to P-type and E-type according to light-emitting mechanism. The P-type delayed fluorescence cannot provide an internal quantum efficiency of 100% since it occurs through triplet-triplet annihilation (TTA). Since the E-type delayed fluorescence is activated by heat energy, it is known as thermally activated delayed fluorescence. According to E-type delayed fluorescence, when the difference between the energy of singlet exciton state and the energy of triplet exciton state ($\Delta E_{ST}$) is low, preferably when lower than 0.2 eV, the singlet exciton emits light as normal, i.e. fluorescence, and the triplet exciton emits light by reverse-intersystem crossing to a singlet exciton, i.e. delayed fluorescence. Hence, in the E-type delayed fluorescence, since a light-emission of a delayed fluorescence is added to a light-emission of a fluorescent mechanism, it is regarded that increasing the internal quantum efficiency to 100% would be possible. In addition, even at a low temperature of lower than 100° C., when using a compound emitting strong fluorescence and delayed fluorescence, a triplet exciton can be sufficiently subjected to reverse-intersystem crossing to a singlet exciton from the heat occurred from the device, thereby emitting light by delayed fluorescence. Thus, the luminous efficiency can be rapidly increased. However, the light-emitting compounds of delayed fluorescence reported until now still have high $\Delta E_{ST}$. Thus, it is difficult to obtain high luminous efficiency.

Korean Patent No. 1317923, Korean Patent Application Laying-Open Nos. 2014-0064655 and 2015-0009512, U.S. Patent Application Publication No. 2014-0131665, and International Publication No. WO 2014/092083 disclose compounds comprising a nitrogen-containing heteroaryl such as triazine or an amine as luminescent compounds for delayed fluorescence. However, these compounds still show low luminous efficiency.

DISCLOSURE OF THE INVENTION

Problems to be Solved

An objective of the present invention is to provide a luminescent material for delayed fluorescence, which can produce an organic electroluminescent device having long lifespan, low driving voltage, high color purity, and significantly improved luminous efficiency such as current efficiency. Another objective is to provide an organic electroluminescent device comprising the luminescent material for delayed fluorescence.

Solution to Problems

The present inventors found that the objective above can be achieved by a compound represented by the following formula 1 as a luminescent material for delayed fluorescence which shows excellent luminous efficiency. Accordingly, the present invention provides the luminescent material for delayed fluorescence comprising the compound represented by the following formula 1 as an embodiment.

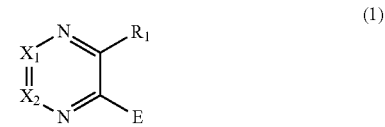

(1)

wherein
R₁ represents a substituted or unsubstituted (C1-C30) alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s)

may be replaced with at least one heteroatom selected from nitrogen, oxygen, sulfur, Si, PO, SO, $SO_2$, and $SeO_2$;

$X_1$ represents —$CR_3$ or N;

$X_2$ represents —$CR_6$ or N;

$R_3$ and $R_6$ each independently represent hydrogen, deuterium, a substituted or unsubstituted (C1-C30)alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

E is represented by the following formula 2 or 3:

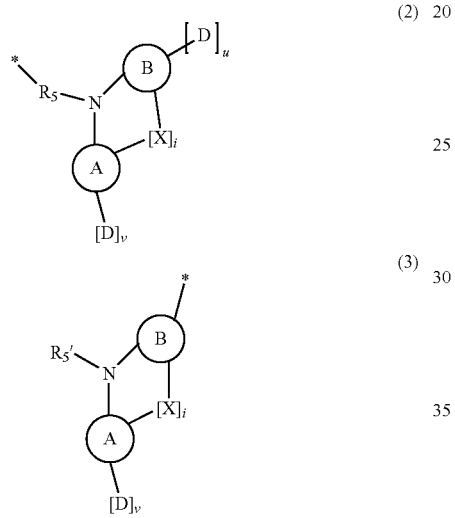

wherein ring A and ring B each independently represent a (C5-C30)aryl, or a 5- to 30-membered heteroaryl;

X is independently selected from a single bond, O, S, $NR_4$, $Si(R_4)_2$, $C(R_4)_2$, $PO(R_4)_2$, SO, $SO_2$, and $SeO_2$;

i represents an integer of 1 or 2; where i is 2, each of X may be the same or different;

$R_4$ represents a substituted or unsubstituted (C1-C30) alkyl, a substituted or unsubstituted (C5-C30)aryl, or a substituted or unsubstituted 5- to 30-membered heteroaryl;

where there are two $R_4$'s, each of the two $R_4$'s may be the same or different, and the two $R_4$'s may be linked to each other to form a substituted or unsubstituted 11- to 60-membered polycyclic ring;

$R_5$ represents a single bond, a substituted or unsubstituted (C5-C30)arylene, or a substituted or unsubstituted 5- to 30-membered heteroarylene; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

$R_5$' represents hydrogen, a substituted or unsubstituted (C5-C30)aryl, or a substituted or unsubstituted 5- to 30-membered heteroaryl; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

D represents a substituted or unsubstituted mono- or di-(C5-C30)arylamino, a substituted or unsubstituted (C5-C30)aryloxy, a substituted or unsubstituted (C5-C30)arylthio, a substituted or unsubstituted (C5-C30) aryl, or a substituted or unsubstituted 5- to 30-membered heteroaryl; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

u and v each independently represent an integer of 0 to 1; where u and v are both 1, each of D may be the same or different; and represents a bonding site between the ring comprising $X_1$ and $X_2$, and E.

Effects of the Invention

By using the luminescent material for delayed fluorescence according to the present invention, an organic electroluminescent device having long lifespan, low driving voltage, excellent color purity, and significantly improved luminous efficiency such as current efficiency is provided.

EMBODIMENTS OF THE INVENTION

Figure 1:
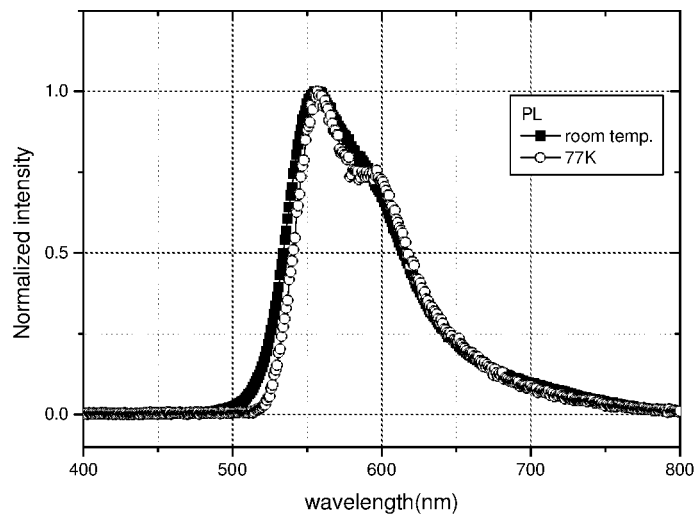
FIG. 1 illustrates a photoluminescence spectrum at low temperature of compound D-2 of Example 1.

Hereinafter, the present invention will be described in detail. However, the following description is intended to explain the invention, and is not meant in any way to restrict the scope of the invention.

According to one embodiment of the present invention, a luminescent material for delayed fluorescence comprising a compound represented by formula 1 is provided.

In the present disclosure, "a luminescent material for delayed fluorescence" means a material used for emitting light by delayed fluorescence.

Hereinafter, the compound represented by formula 1 of the present invention will be specifically described in detail.

Herein, "(C1-C30)alkyl(ene)" is meant to be a linear or branched alkyl(ene) having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tertbutyl, etc.; "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "3- to 7-membered heterocycloalkyl" is a cycloalkyl having 3 to 7 ring backbone atoms, preferably 5 to 7, including at least one heteroatom selected from B, N, O, S, Si, and P, preferably O, S, and N, and includes tetrahydrofuran, pyrrolidine, thiolan, tetrahydropyran, etc.; "(C5-C30)aryl(ene)" is a monocyclic or fused ring derived from an aromatic hydrocarbon having 5 to 30 ring backbone carbon atoms, in which the number of carbon atoms is preferably 5 to 20, more preferably 6 to 15, including substituents having a spiro structure, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, cyclopentadienyl, indenyl, triphenylenyl, pyrenyl, tetracenyl, perylenyl, chrysenyl, naphthacenyl, fluoranthenyl, spirobifluorenyl, etc.; "5- to 30-membered heteroaryl(ene)" is an aryl having 5 to 30 ring backbone atoms, including at least one, preferably 1 to 4 heteroatoms selected from the group consisting of B, N, O, S, Si, and P; is a monocyclic ring, or a fused ring condensed with at least one benzene ring; may be partially saturated; may be one formed by linking at least one heteroaryl or aryl group to a heteroaryl group via a single bond(s); including substituents having a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, carbolinyl, acridinyl, phenoxazinyl, phenothiazinyl, phenanthridinyl, benzodioxolyl, dihydroacridinyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl, the substituted alkenyl, the substituted aryl(ene), the substituted heteroaryl(ene), the substituted fused ring, the substituted mono-arylamino, and the substituted di-arylamino in $R_1$, $R_3$, $R_4$, $R_5$, $R_5'$, $R_6$, $R_7$, $R_5$, $R_{11}$, D, R, and L each independently are at least one selected from the group consisting of deuterium, a halogen, a cyano, a carboxyl, a nitro, a hydroxyl, a (C1-C30)alkyl, a halo(C1-C30)alkyl, a (C2-C30) alkenyl, a (C2-C30) alkynyl, a (C1-C30)alkoxy, a (C3-C30)cycloalkyl, a 3- to 7-membered heterocycloalkyl, a (C5-C30)aryloxy, a 3- to 30-membered heteroaryl unsubstituted or substituted with a (C5-C30)aryl, a (C5-C30)aryl unsubstituted or substituted with a 3- to 30-membered heteroaryl, a tri(C1-C30)alkylsilyl, a tri(C5-C30)arylsilyl, a di(C1-C30)alkyl(C5-C30)arylsilyl, a (C1-C30)alkyldi(C5-C30)arylsilyl, an amino, a mono- or di-(C1-C30)alkylamino, a mono- or di-(C5-C30)arylamino, a (C1-C30)alkyl(C5-C30)arylamino, a (C1-C30)alkylcarbonyl, a (C1-C30)alkoxycarbonyl, a (C5-C30)arylcarbonyl, a di(C5-C30)arylboronyl, a di(C1-C30)alkylboronyl, a (C1-C30)alkyl(C5-C30)arylboronyl, a (C5-C30)aryl(C1-C30)alkyl, and a (C1-C30)alkyl(C5-C30)aryl.

The compound of formula 1 can be preferably represented by the following formula 4 or 5:

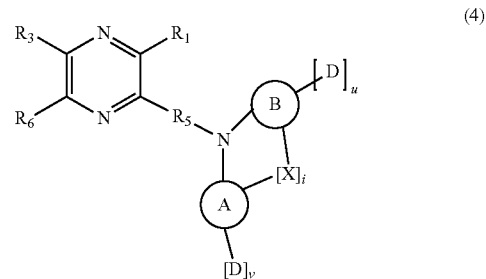

(4)

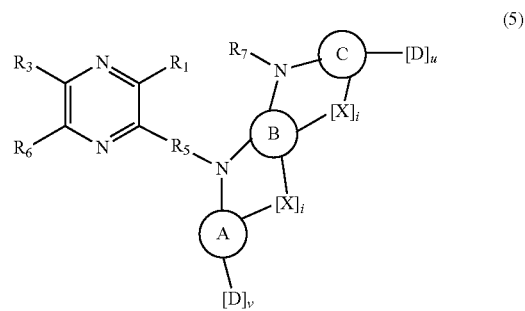

(5)

wherein $R_1$ represents a substituted or unsubstituted (C5-C20)aryl, or a substituted or unsubstituted 5- to 20-membered heteroaryl;

$R_5$ represents a single bond, a substituted or unsubstituted (C5-C20)arylene, or a substituted or unsubstituted 5- to 20-membered heteroarylene;

$R_7$ represents hydrogen, deuterium, a substituted or unsubstituted (C1-C20)alkyl, a substituted or unsubstituted (C2-C20)alkenyl, a substituted or unsubstituted (C5-C20)aryl, a substituted or unsubstituted 5- to 20-membered heteroaryl, or CN;

ring C represents a (C5-C30)aryl, or a 5- to 30-membered heteroaryl; and $R_3$, $R_6$, ring A, ring B, X, D, i, v, and u are as defined in formula 1.

Preferably, formulas 4 and 5 can be respectively represented by the following formulas 6 and 7:

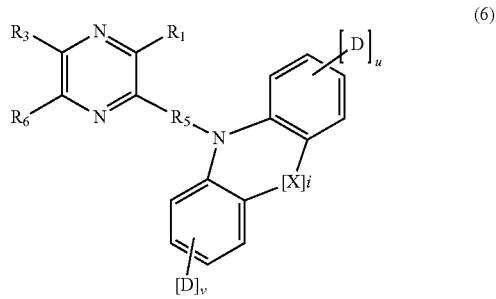

(6)

-continued

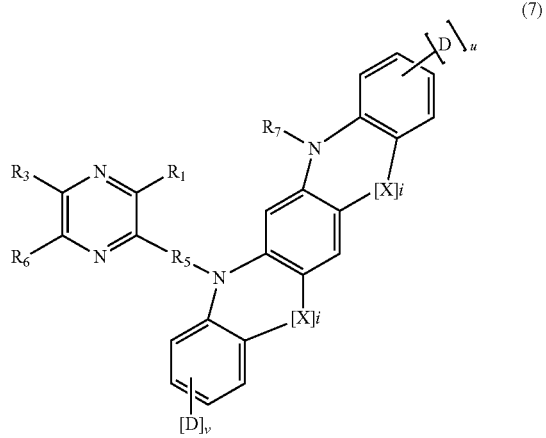
(7)

wherein $R_1$, $R_3$, $R_5$, $R_6$, $R_7$, X, D, i, u, and v are as defined in formulas 4 and 5.

In formulas 1, 4, 5, 6, and 7 above, $R_1$ preferably represents a substituted or unsubstituted (C5-C20)aryl, or a substituted or unsubstituted 5- to 20-membered heteroaryl; more preferably represents a substituted or unsubstituted phenyl, a substituted or unsubstituted biphenyl, a substituted or unsubstituted naphthyl, a substituted or unsubstituted pyrrolyl, a substituted or unsubstituted pyridyl, a substituted or unsubstituted indolyl, a substituted or unsubstituted carbazolyl, a substituted or unsubstituted benzofuranyl, a substituted or unsubstituted benzothiophenyl, a substituted or unsubstituted dibenzofuranyl, or a substituted or unsubstituted dibenzothiophenyl; and even more preferably represents a substituted or unsubstituted phenyl, a substituted or unsubstituted biphenyl, a substituted or unsubstituted naphthyl, a substituted or unsubstituted pyrrolyl, or a substituted or unsubstituted pyridyl;

$X_1$ preferably represents —$CR_3$;

$X_2$ preferably represents —$CR_6$;

$R_3$ and $R_6$ preferably each independently represent hydrogen, a substituted or unsubstituted (C5-C20)aryl, or a substituted or unsubstituted 5- to 20-membered heteroaryl; or may be linked to an adjacent substituent to form a substituted or unsubstituted mono- or polycyclic, (C5-C30) alicyclic or aromatic ring, whose carbon atom(s) may be replaced with at least one selected from nitrogen, oxygen, sulfur, Si, PO, SO, $SO_2$, and $SeO_2$; and more preferably each independently represent a substituted or unsubstituted phenyl, a substituted or unsubstituted biphenyl, a substituted or unsubstituted naphthyl, a substituted or unsubstituted pyrrolyl, a substituted or unsubstituted pyridyl, a substituted or unsubstituted indolyl, a substituted or unsubstituted carbazolyl, a substituted or unsubstituted benzofuranyl, a substituted or unsubstituted benzothiophenyl, a substituted or unsubstituted dibenzofuranyl, or a substituted or unsubstituted dibenzothiophenyl; or may be linked to an adjacent substituent to form a substituted or unsubstituted polycyclic, (C5-C20) aromatic ring, whose carbon atom(s) may be replaced with at least one selected from nitrogen, oxygen, and sulfur;

E is preferably represented by formula 2;

ring A and ring B preferably each independently represent a (C5-C20)aryl, or a 5- to 20-membered heteroaryl; and more preferably each independently represent a benzene ring; a naphthalene ring, a pyridine ring, a benzothiophene ring, or a benzofuran ring;

X is preferably independently selected from a single bond, O, S, $NR_4$, $Si(R_4)_2$, and $C(R_4)_2$;

i preferably represents 1;

$R_4$ preferably represents a substituted or unsubstituted (C1-C20)alkyl, a substituted or unsubstituted (C5-C20)aryl, or a substituted or unsubstituted 5- to 20-membered heteroaryl;

$R_5$ preferably represents a single bond, a substituted or unsubstituted (C5-C20)arylene, or a substituted or unsubstituted 5- to 20-membered heteroarylene;

$R_5'$ preferably represents hydrogen, a substituted or unsubstituted (C5-C20)aryl, or a substituted or unsubstituted 5- to 20-membered heteroaryl;

D preferably represents a substituted or unsubstituted di-(C5-C20)arylamino, a substituted or unsubstituted (C5-C20)aryloxy, a substituted or unsubstituted (C5-C20)arylthio, a substituted or unsubstituted (C5-C30)aryl, or a substituted or unsubstituted 5- to 30-membered heteroaryl; or may be linked to an adjacent substituent to form a substituted or unsubstituted polycyclic, (C5-C20) aromatic ring, whose carbon atom(s) may be replaced with at least one heteroatom selected from nitrogen, oxygen, and sulfur, and preferably is substituted with a substituent having a property of an electron donor; and more preferably represents a substituted or unsubstituted carbazole, a substituted or unsubstituted benzocarbazole, a substituted or unsubstituted indolocarbazole, a substituted or unsubstituted diphenylamino, a substituted or unsubstituted dinaphthylamino, a substituted or unsubstituted acridinyl, a substituted or unsubstituted phenoxazinyl, a substituted or unsubstituted phenothiazinyl, a substituted or unsubstituted phenoxy, or a substituted or unsubstituted phenylthio; and u+v is preferably 1 or more.

In formulas 4, 5, 6, and 7 above, $R_7$ preferably represents a substituted or unsubstituted (C5-C20)aryl, or a substituted or unsubstituted 5- to 20-membered heteroaryl.

Formula 1 can be preferably selected from the following formulas 1-1 to 1-16:

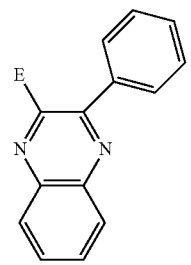
1-1

1-2

-continued
1-3
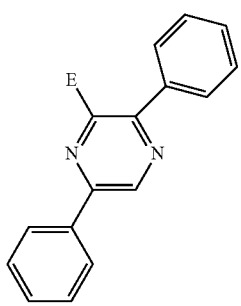
1-4
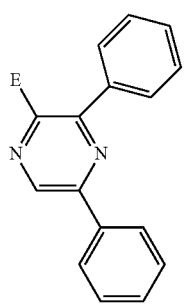
1-5
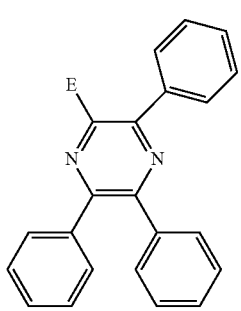
1-6
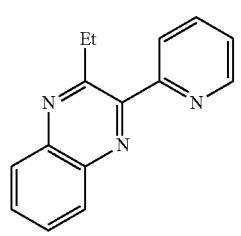
1-7
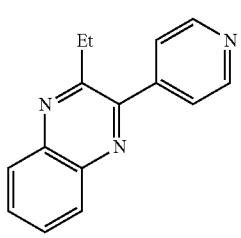
1-8
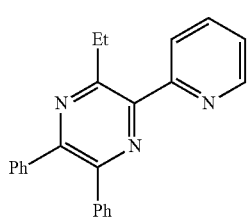
-continued
1-9
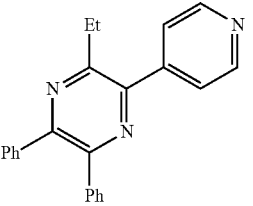
1-10
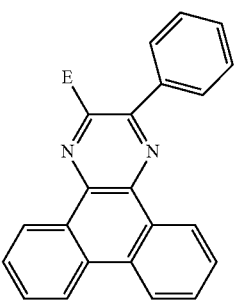
1-11
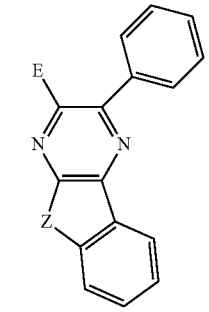
1-12
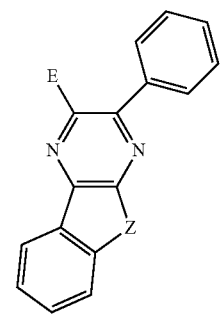
1-13
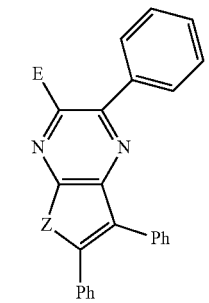

-continued

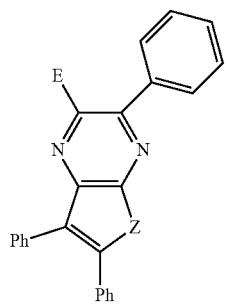

1-14

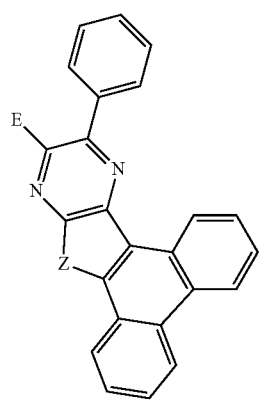

1-15

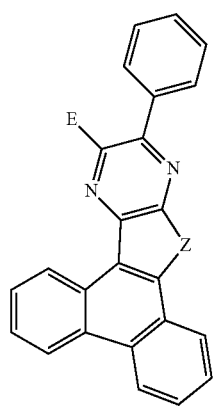

1-16 wherein

Z is selected from O, S, $NR_B$, $Si(R_8)_2$, $C(R_8)_2$, $PO(R_8)_2$, SO, $SO_2$, and $SeO_2$;

$R_8$ represents a substituted or unsubstituted (C1-C30) alkyl, a substituted or unsubstituted (C5-C30)aryl, or a substituted or unsubstituted 5- to 30-membered heteroaryl; and Ph represents phenyl, and E is as defined in formula 1.

In formulas 1 and 1-1 to 1-16 above, E can be preferably represented by formula 2, and formula 2 can be preferably selected from the following formulas 2-1 to 2-35:

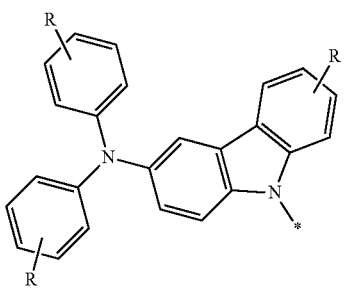

2-1

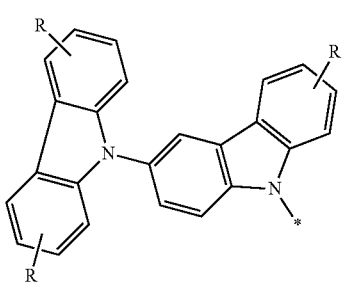

2-2

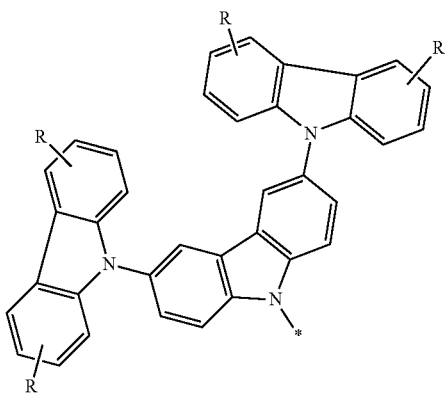

2-3

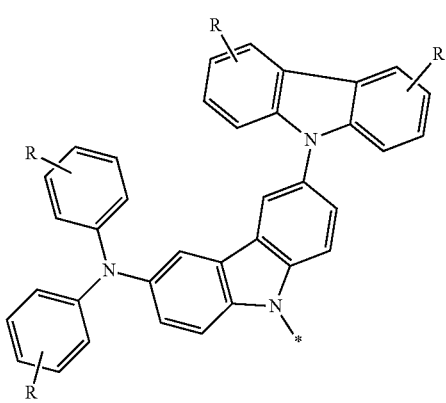

2-4

-continued
2-5
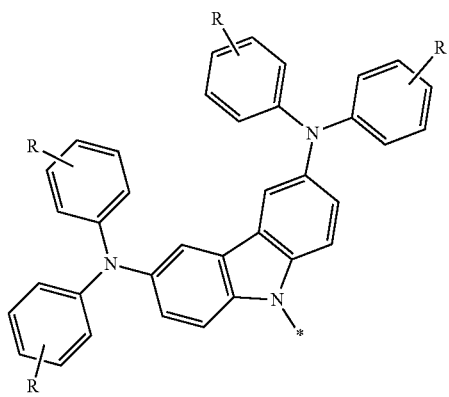
2-6
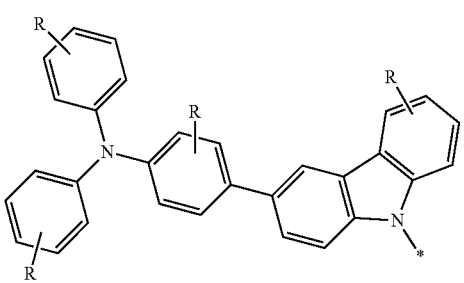
2-7
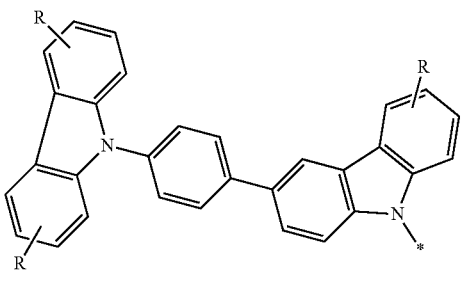
2-8
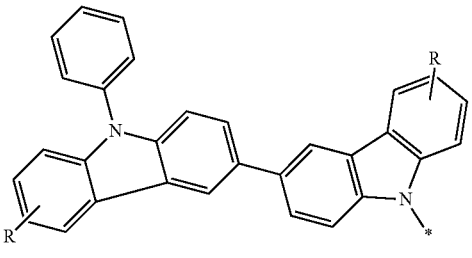
2-9
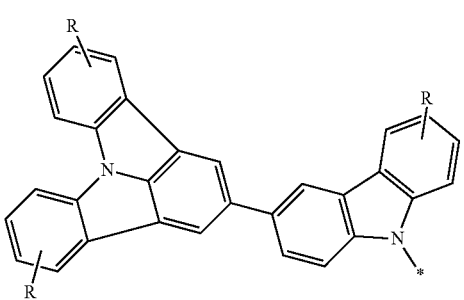
-continued
2-10
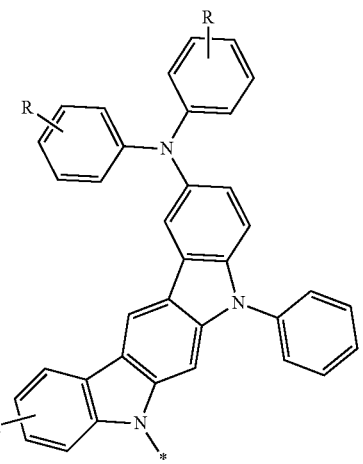
2-11
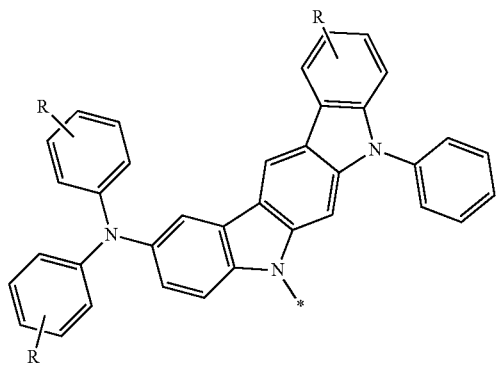
2-12
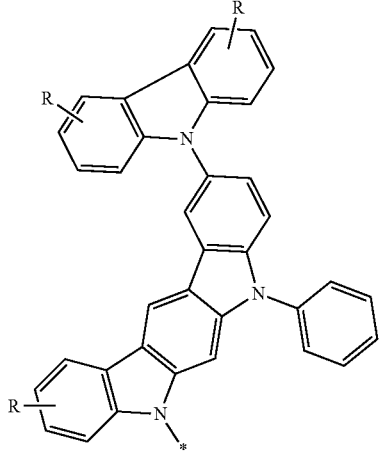
2-13
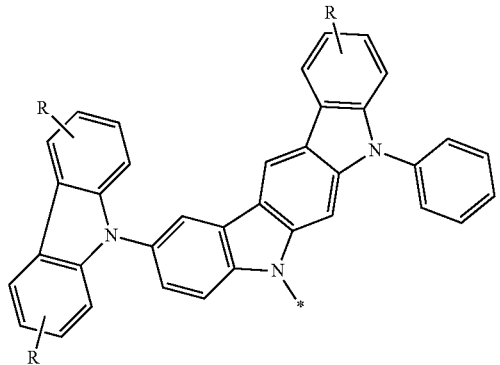

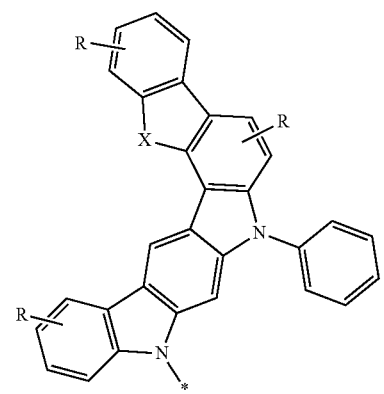
2-14
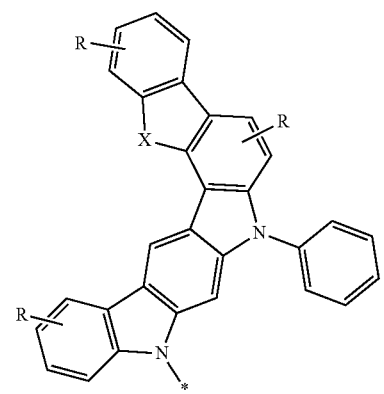
2-15
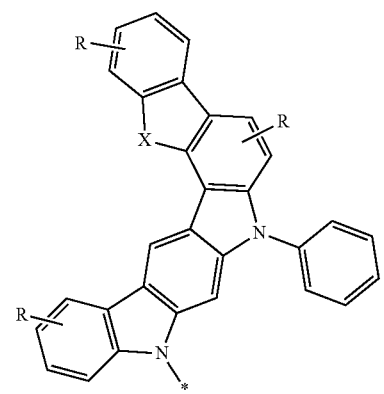
2-16
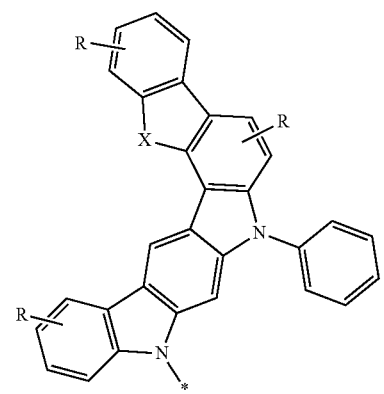
2-17
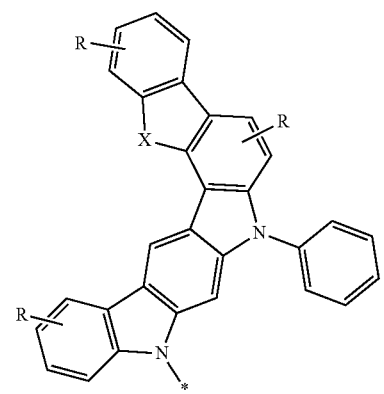
2-18
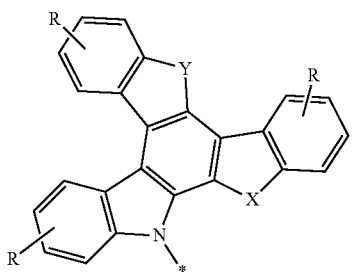
2-19
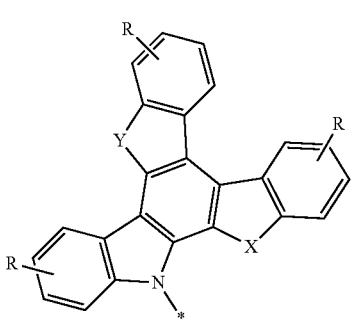
2-20
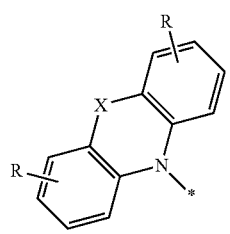
2-21
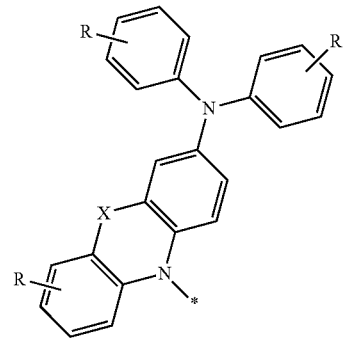
2-22

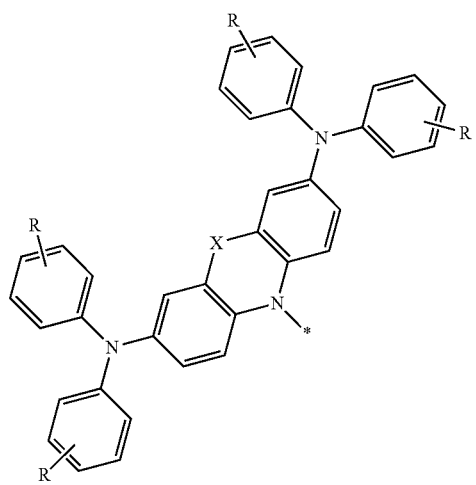
2-23
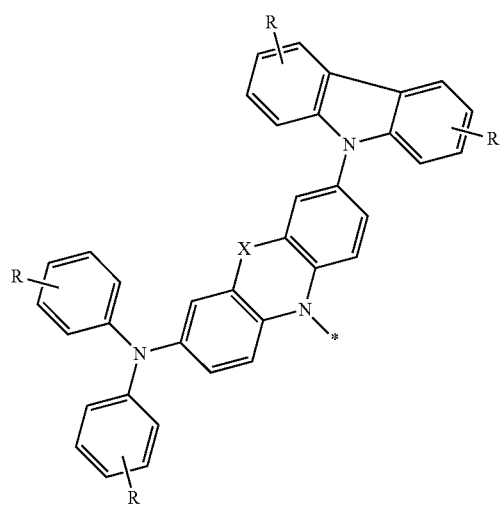
2-26
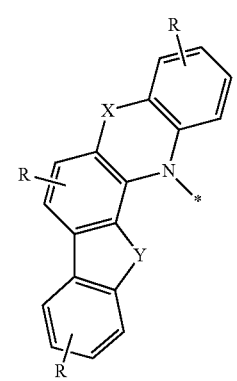
2-24
2-27
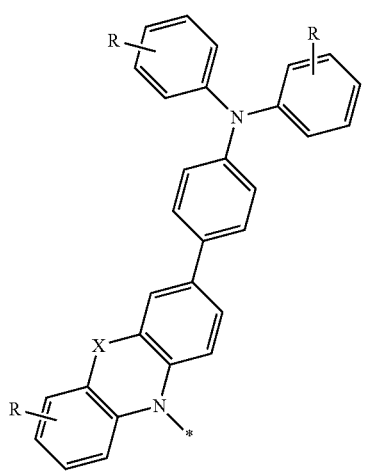
2-25
2-28

2-29
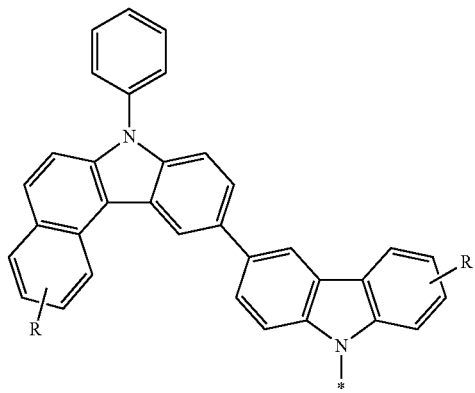

2-33
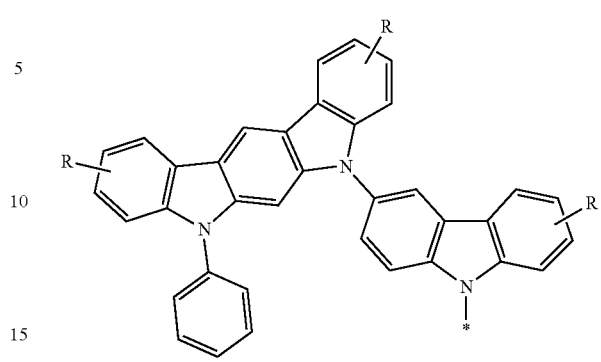

2-30
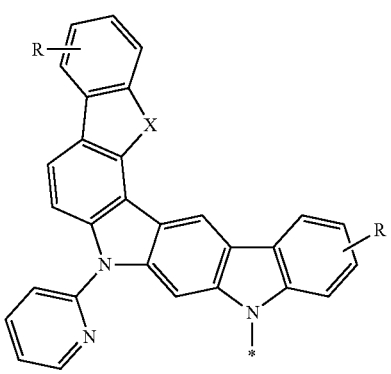

2-34
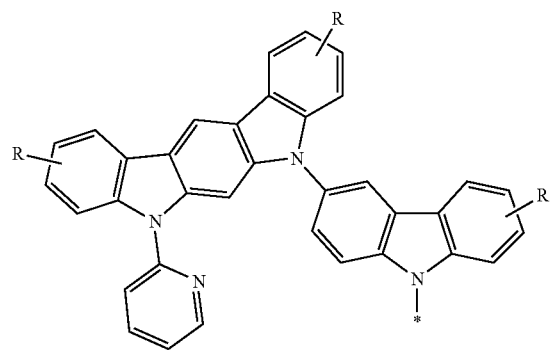

2-31
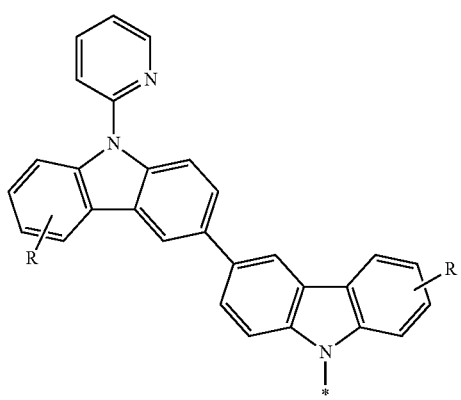

2-35
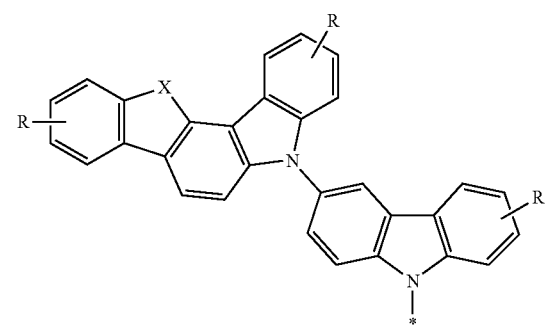

2-32
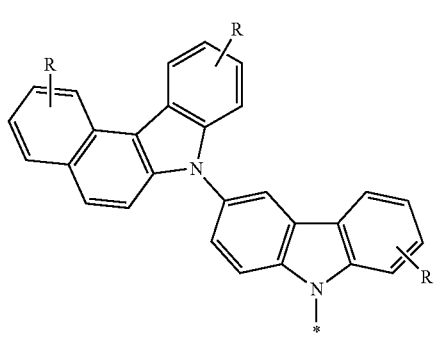

wherein

X and Y each independently are selected from O, S, $NH_4$, $Si(R_4)_2$, $C(R_4)_2$, $PO(R_4)_2$, SO, $SO_2$, and $SeO_2$;

$R_4$ represents a substituted or unsubstituted (C1-C30) alkyl, a substituted or unsubstituted (C5-C30)aryl, or a substituted or unsubstituted 5- to 30-membered heteroaryl; where there are two $R_4$'s, each of the two $R_4$'s may be the same or different, and the two $R_4$'s may be linked to each other to form a substituted or unsubstituted 11- to 60-membered polycyclic ring; and R each independently represents hydrogen, a substituted or unsubstituted (C1-C30)alkyl, a substituted or unsubstituted (C5-C30)aryl, or a substituted or unsubstituted 5- to 30-membered heteroaryl.

The compound represented by formula 1 includes the following compounds, but is not limited thereto:

D-1
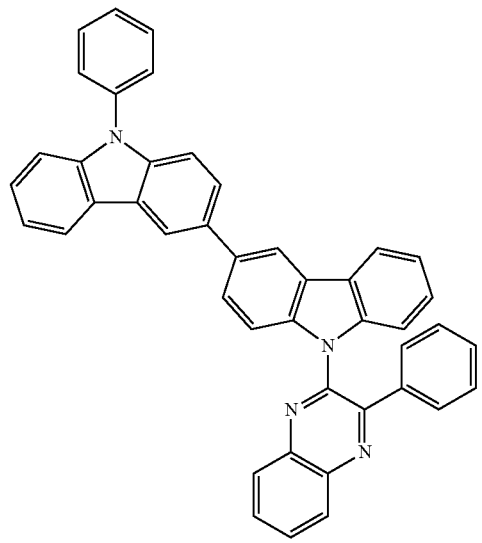
D-4
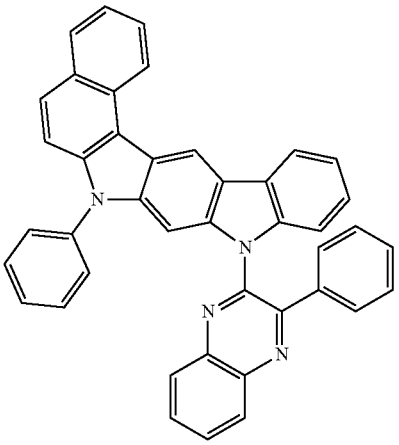
D-2
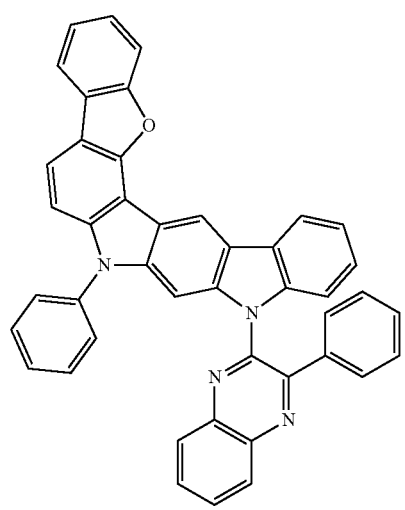
D-5
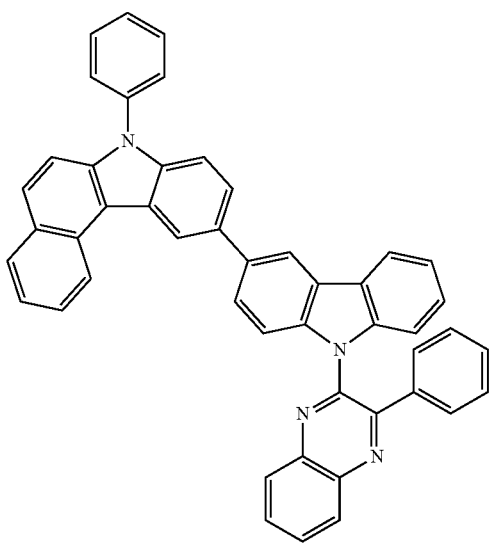
D-3
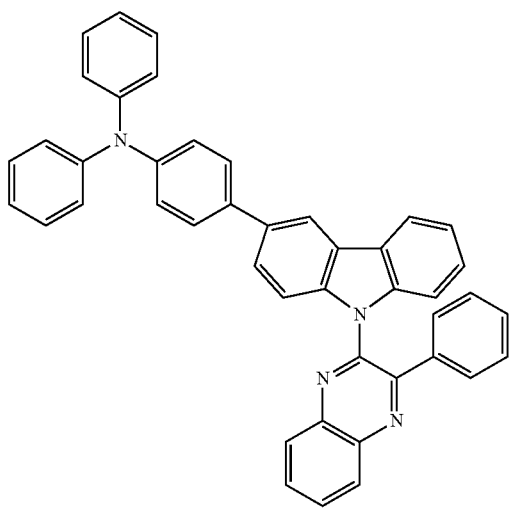
D-6
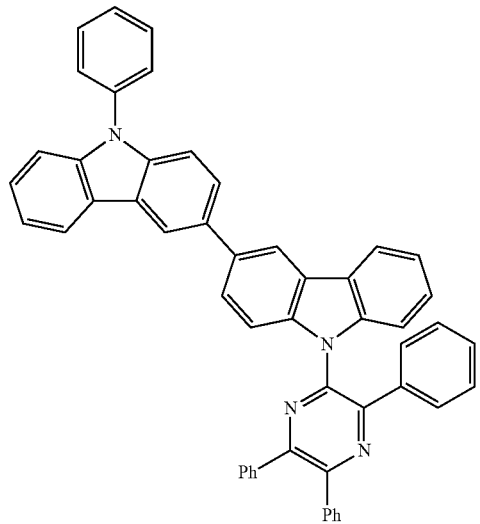

D-7
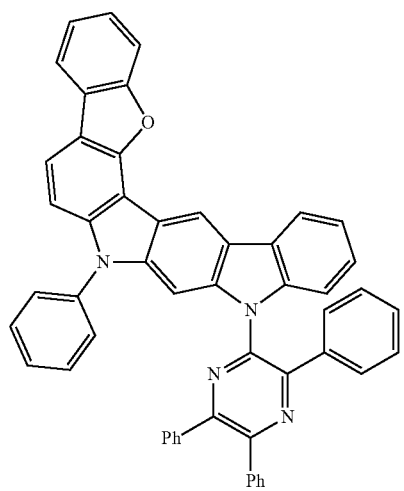
D-8
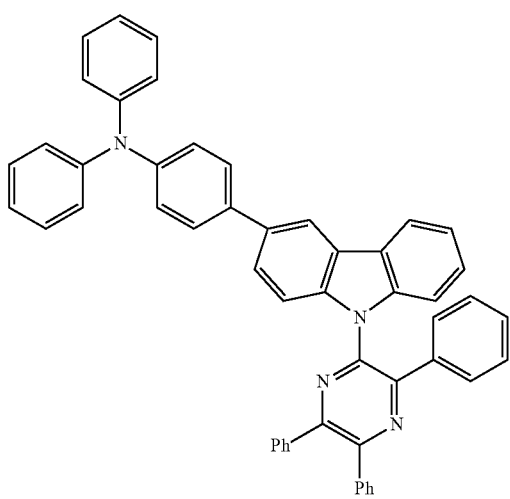
D-9
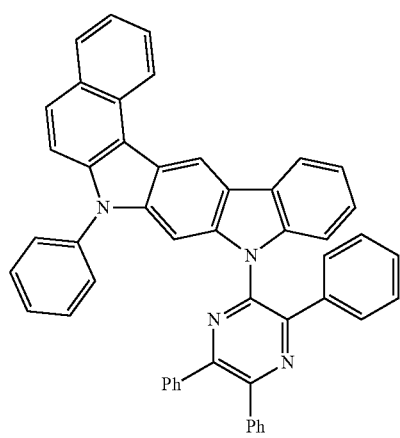
D-10
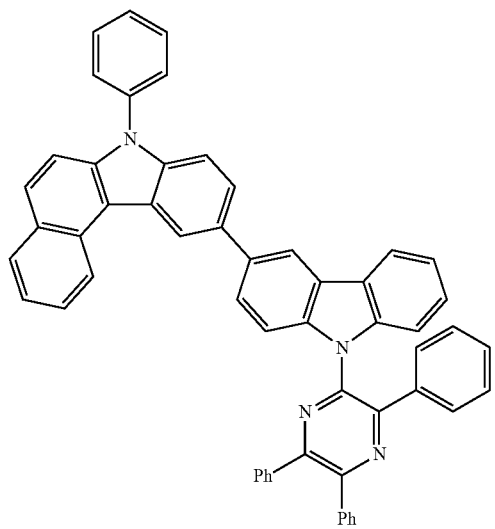
D-11
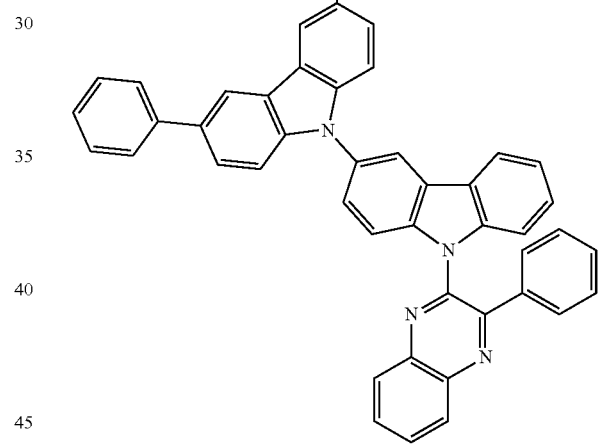
D-12
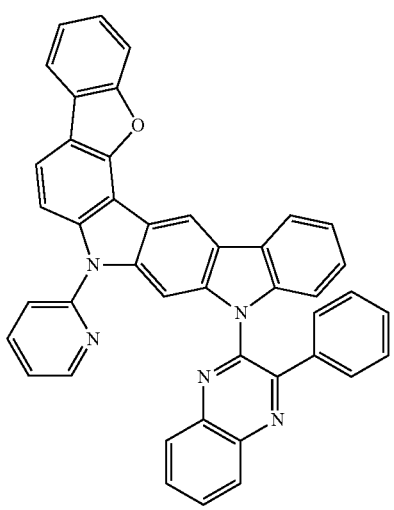

-continued
D-13
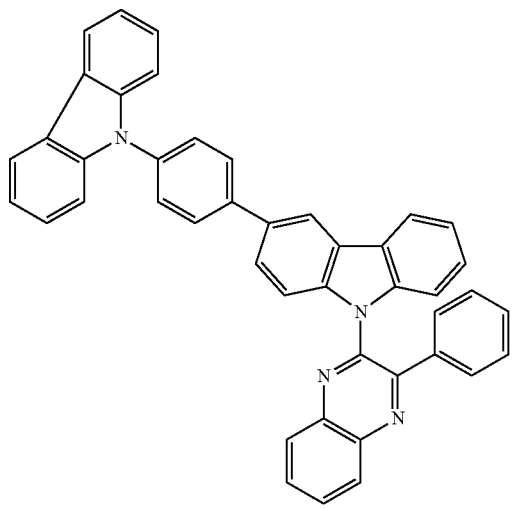
D-14
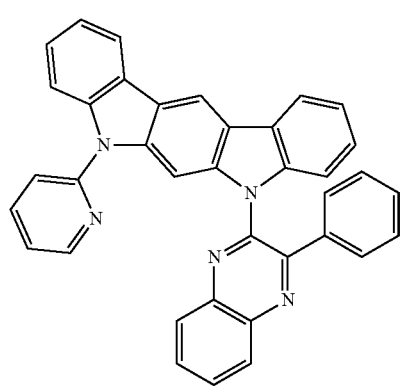
D-15
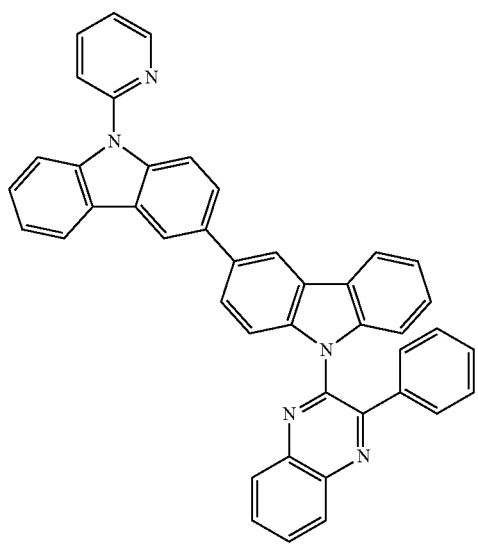
-continued
D-16
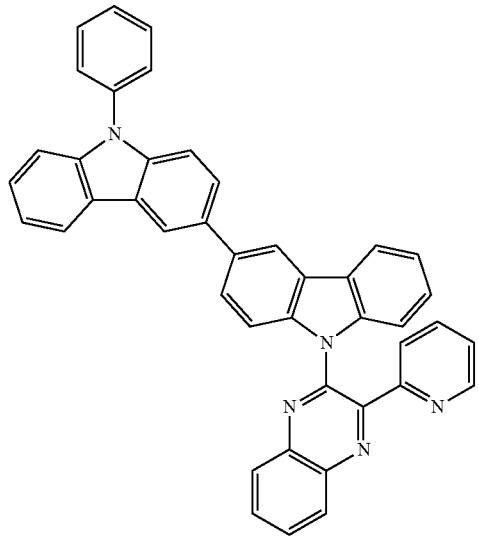
D-17
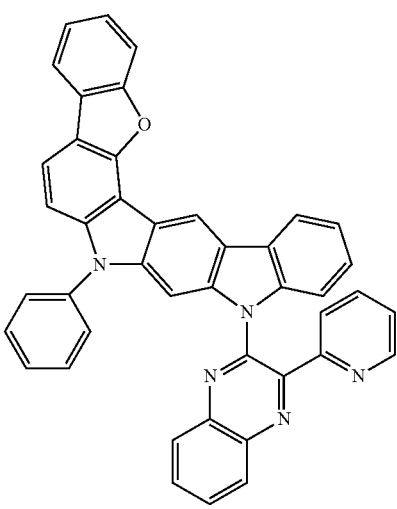
D-18
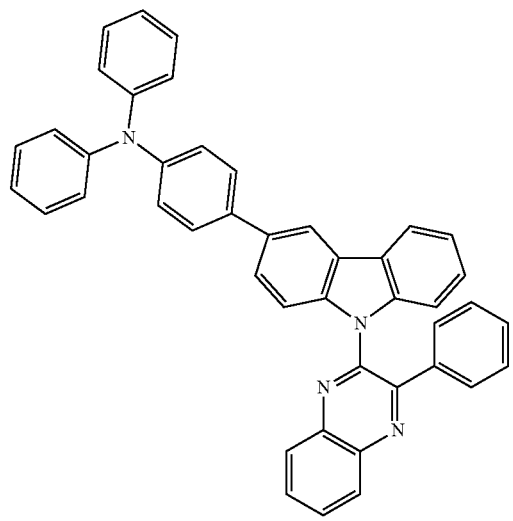

D-19
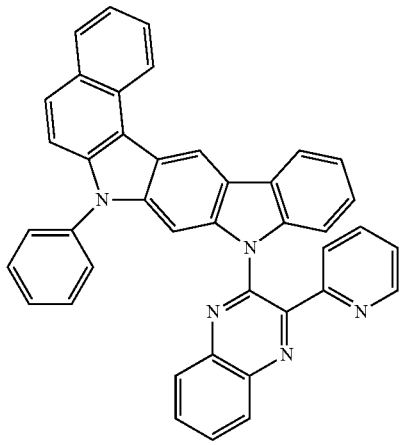
D-20
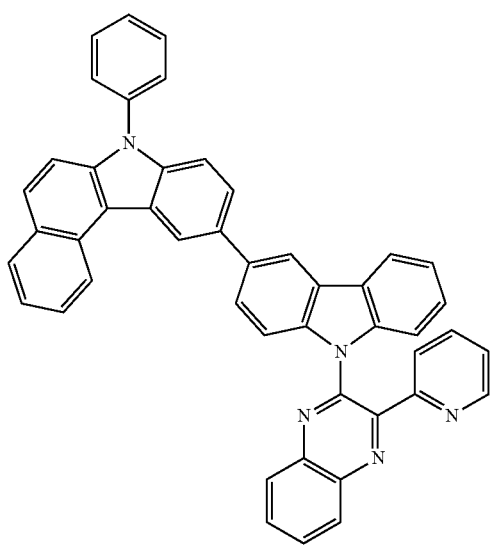
D-21
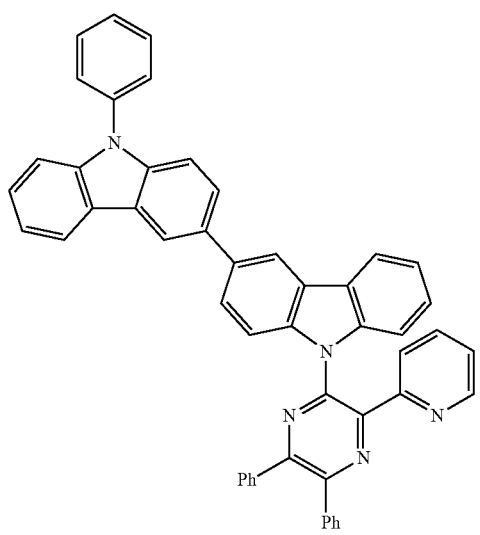
D-22
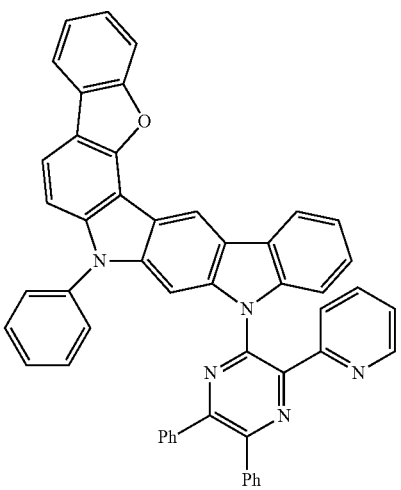
D-23
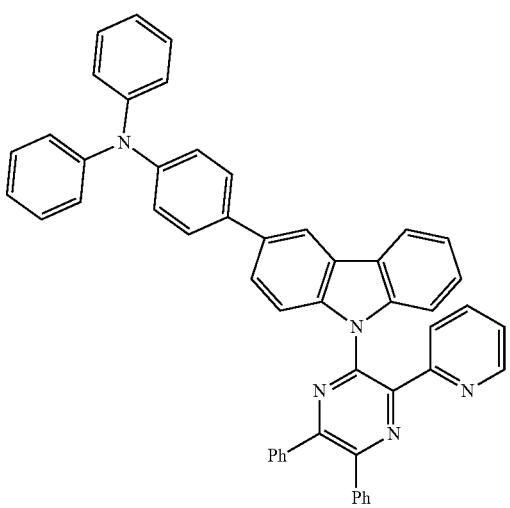
D-24
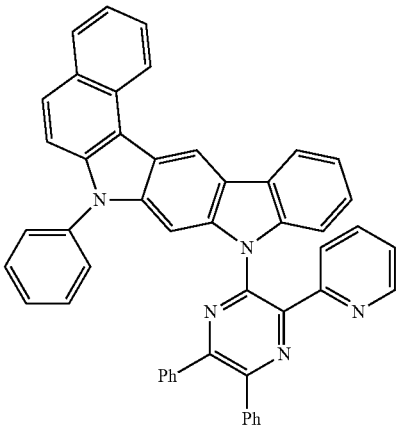

D-25
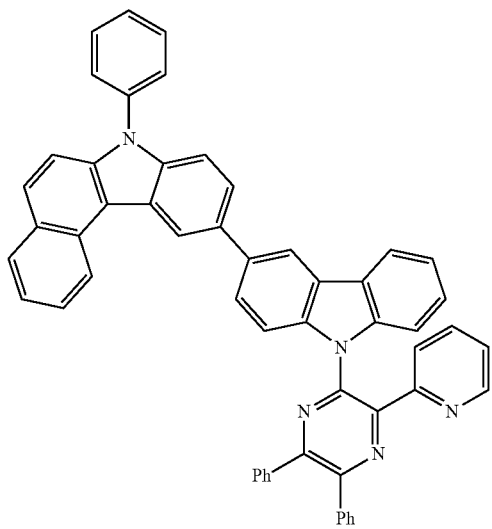
D-26
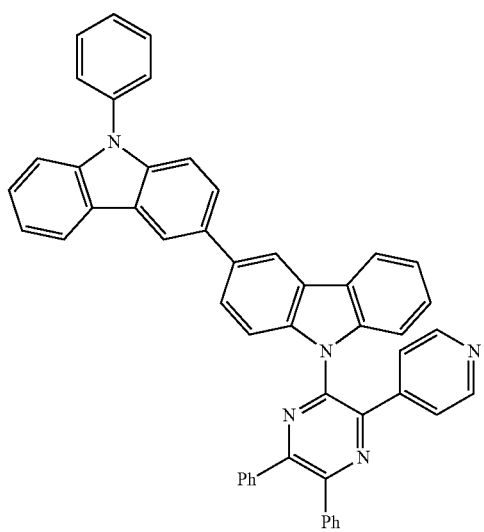
D-27
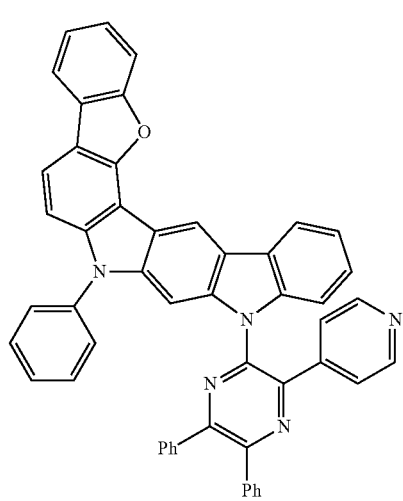
D-28
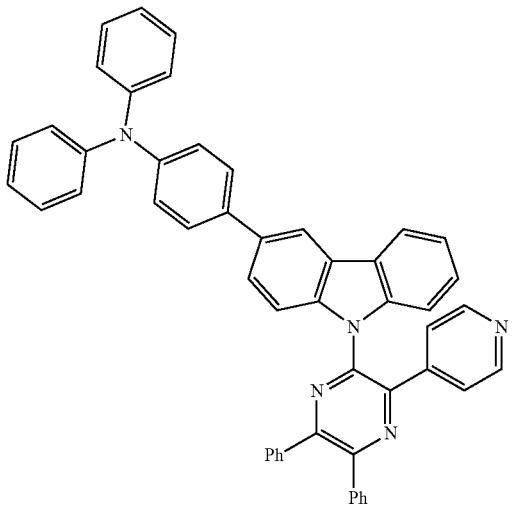
D-29
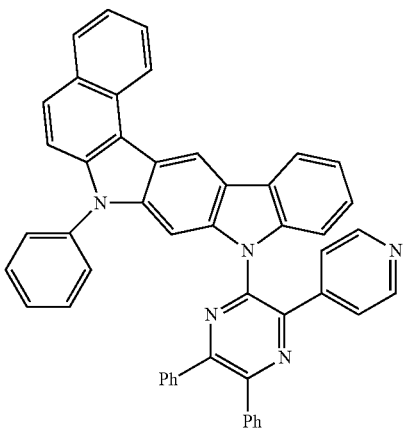
D-30
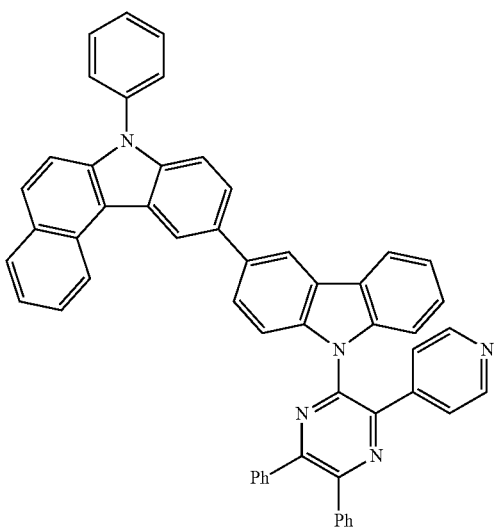

D-31
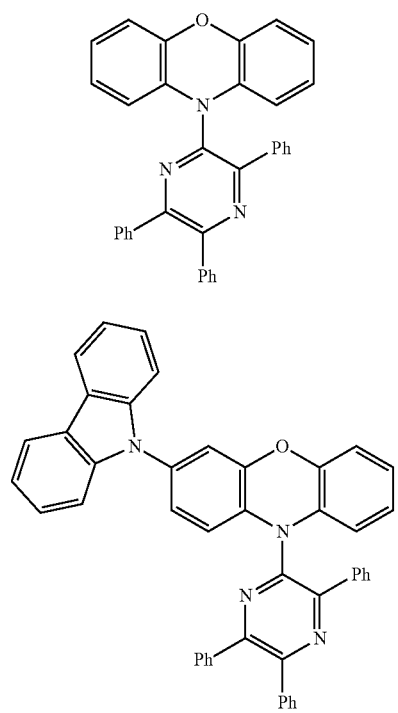
D-32
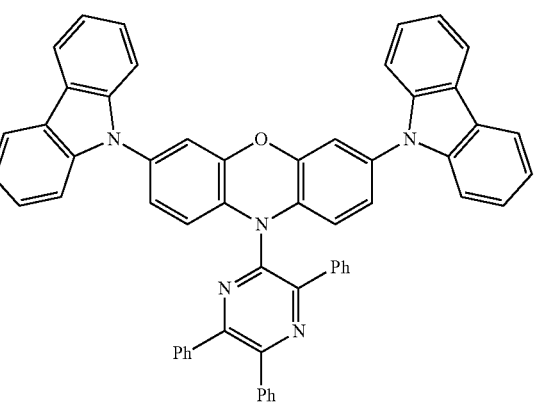
D-33
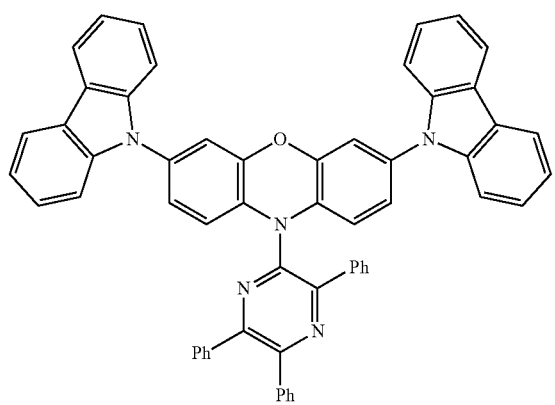
D-34
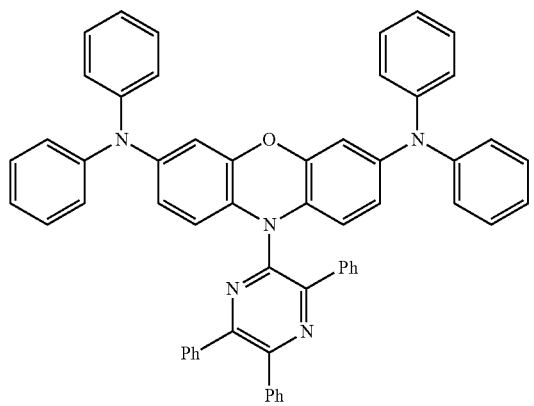
D-35
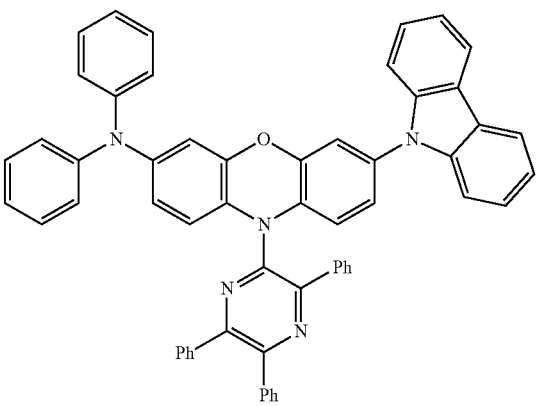
D-36
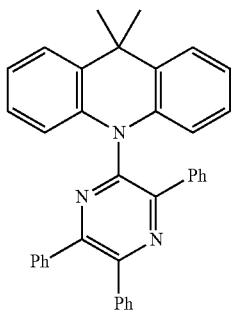
D-37
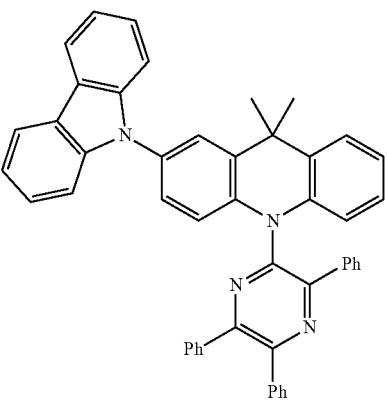
D-38
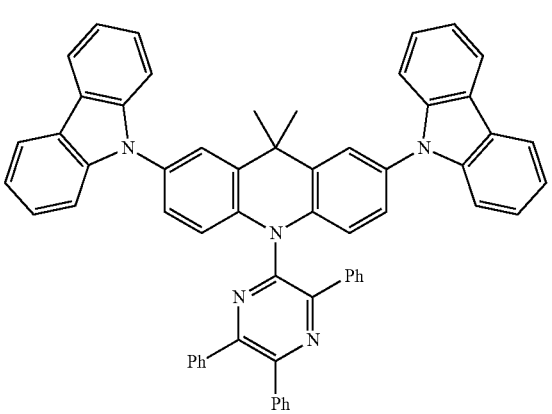

D-39
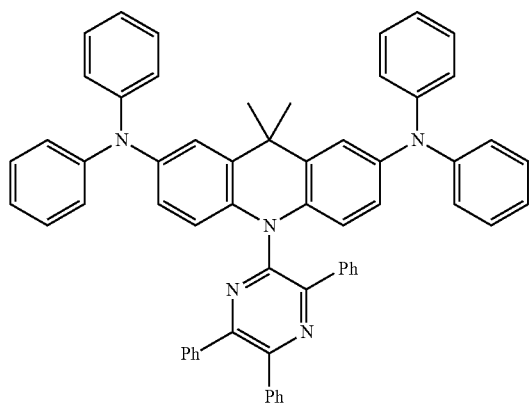
D-42
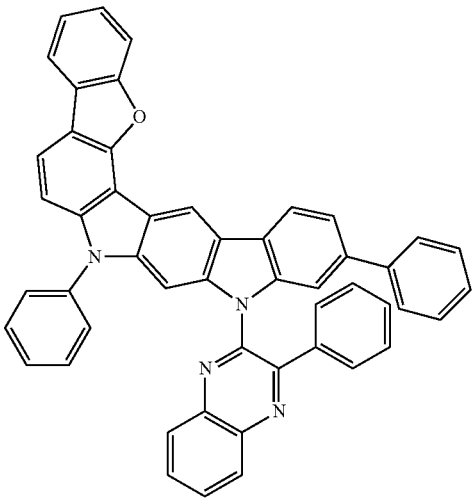
D-40
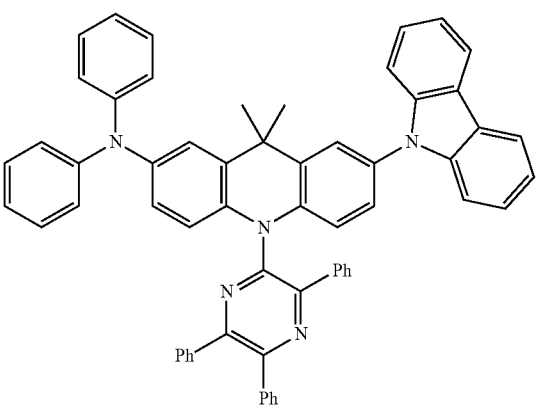
D-43
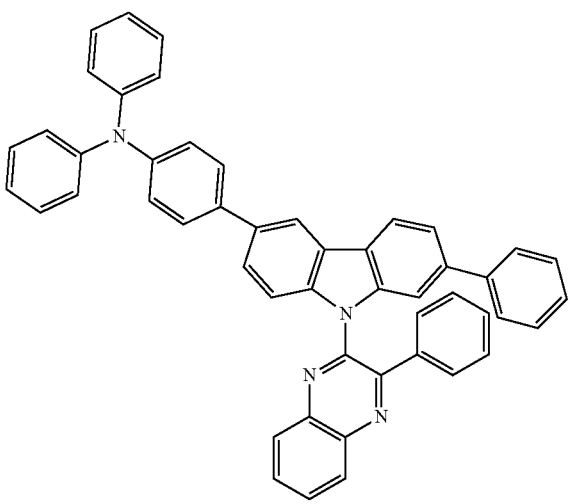
D-41
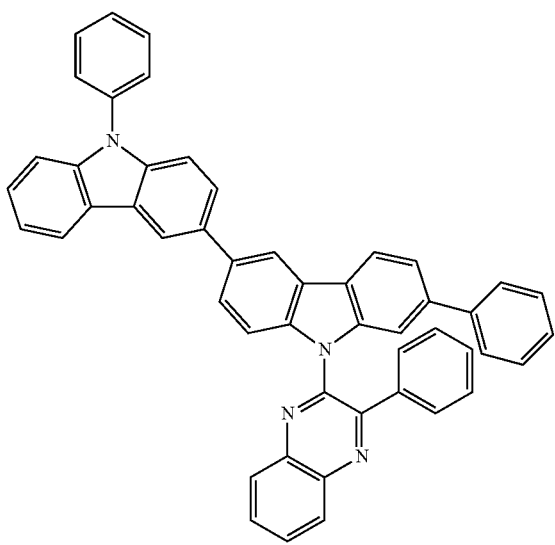
D-44
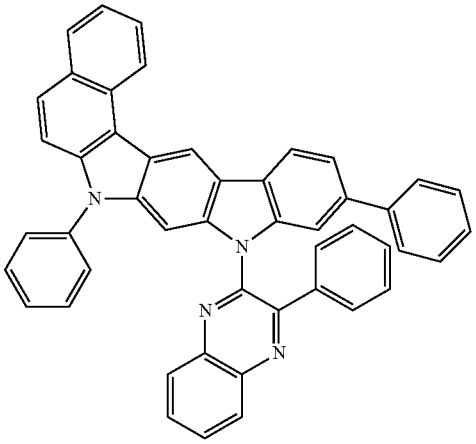

D-45
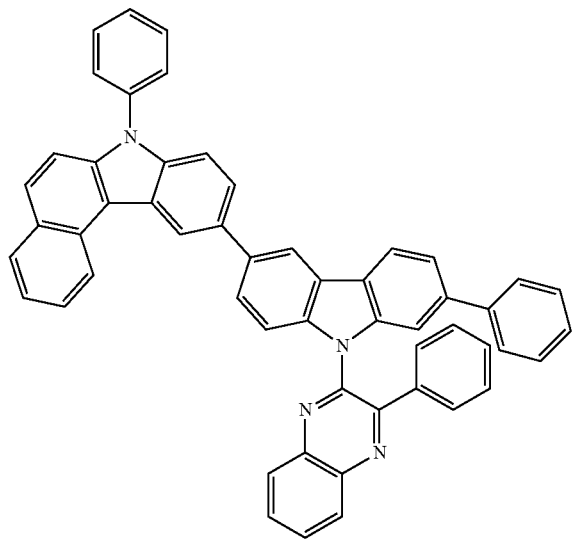
D-46
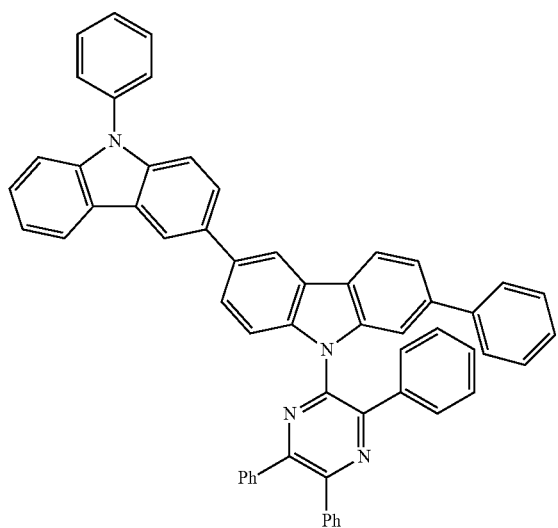
D-47
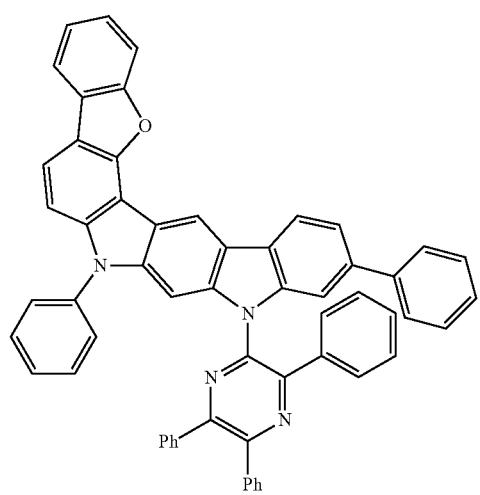
D-48
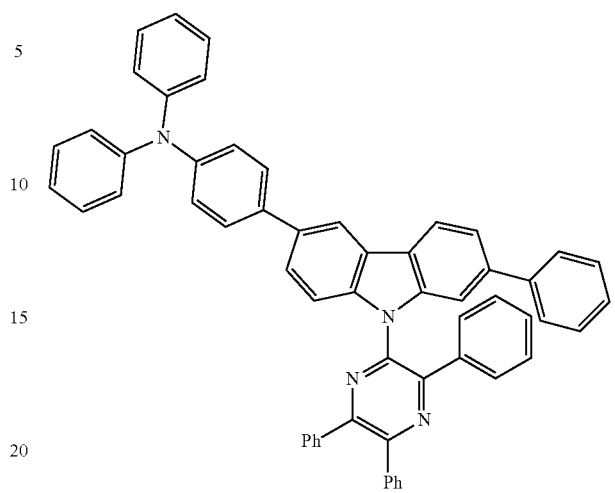
D-49
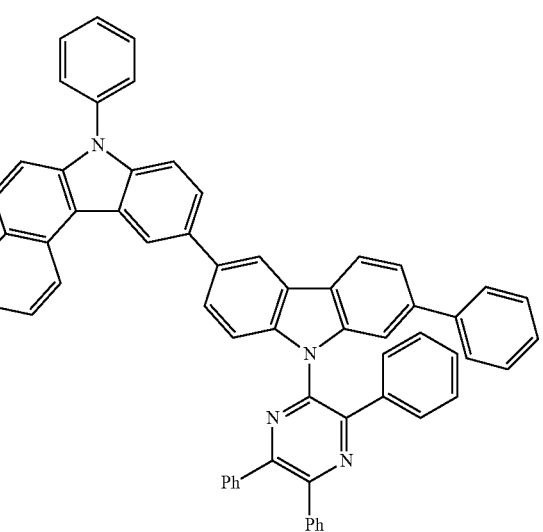
D-50

D-51
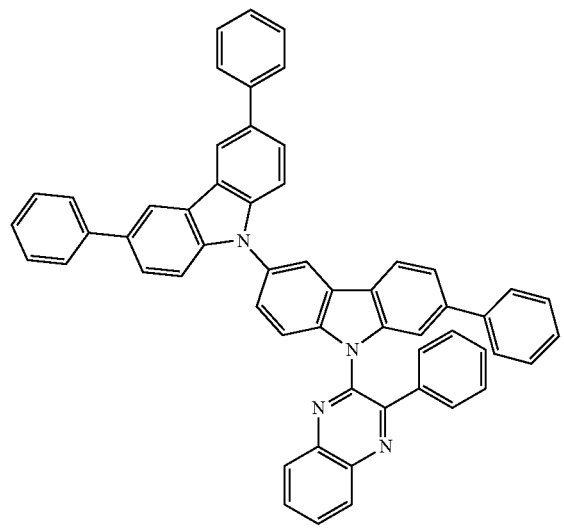
D-52
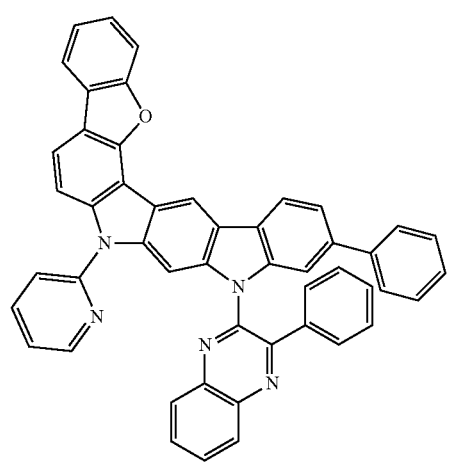
D-53
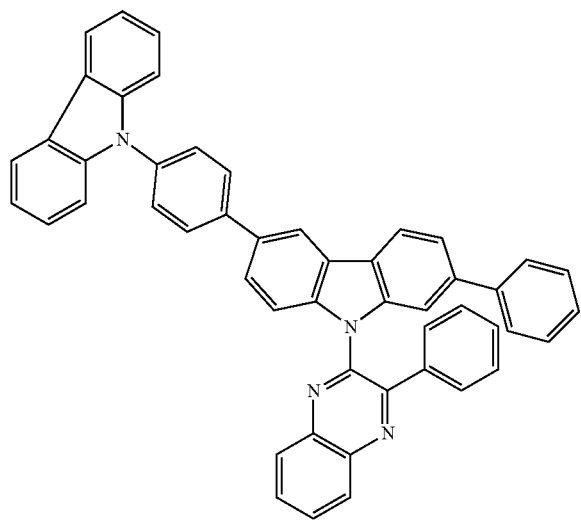
D-54
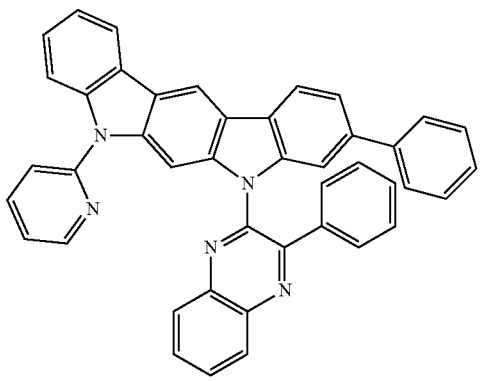
D-55
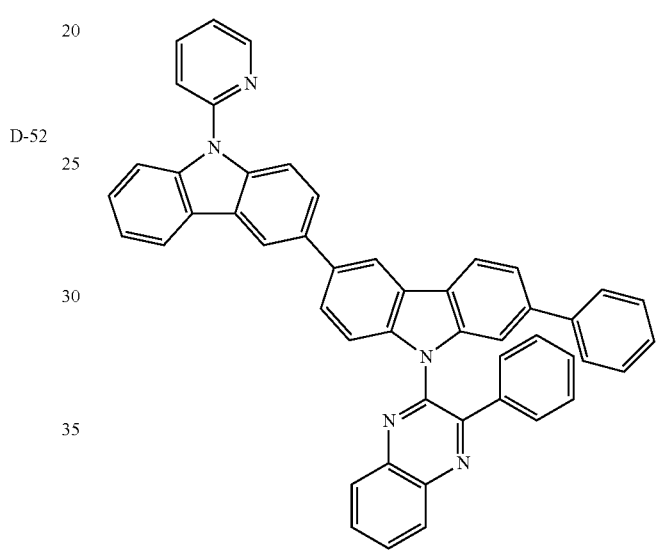
D-56
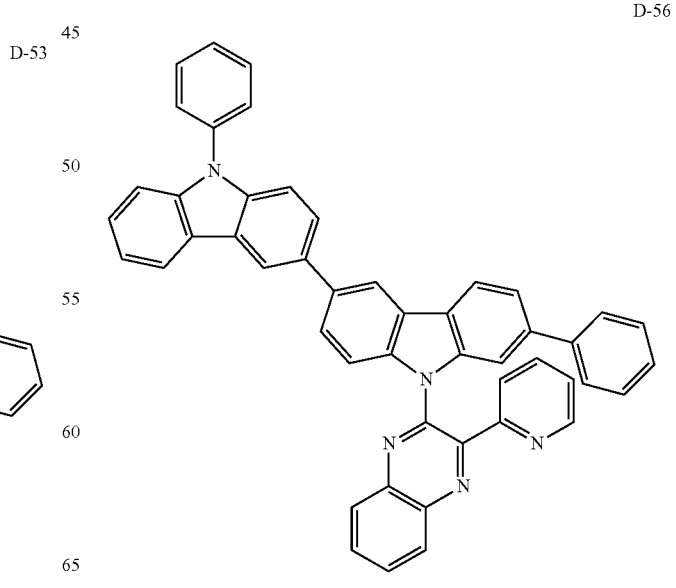

D-57
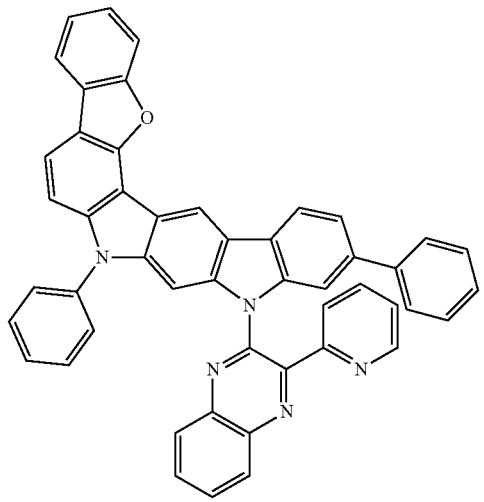
D-60
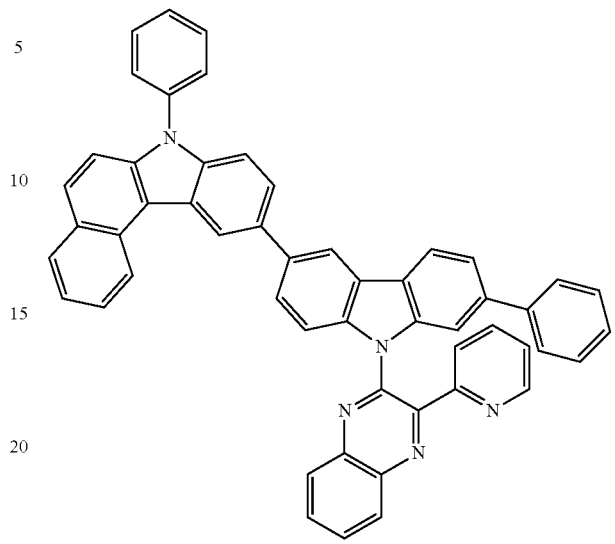
D-58
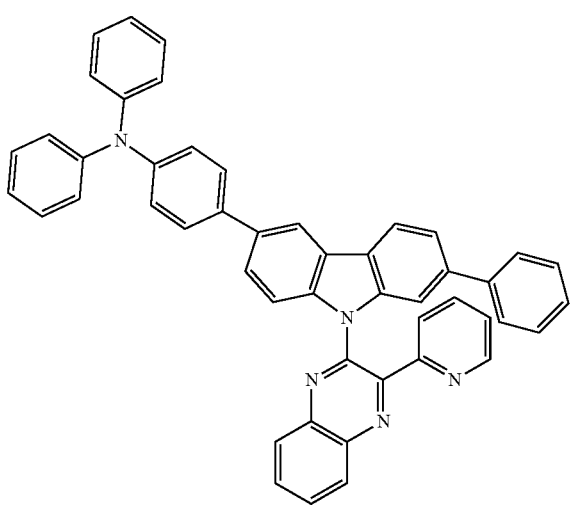
D-61
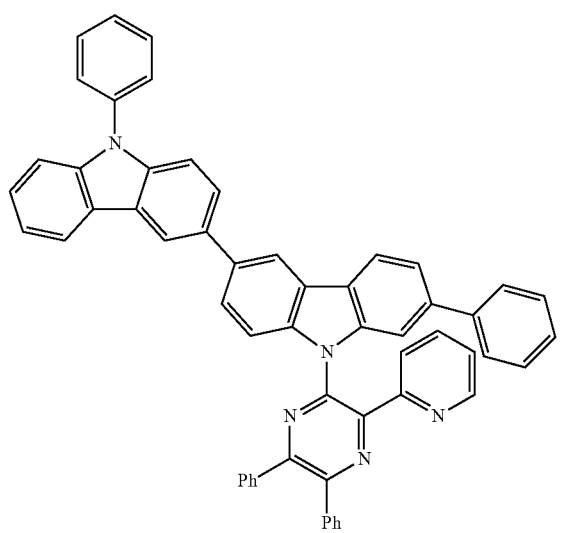
D-59
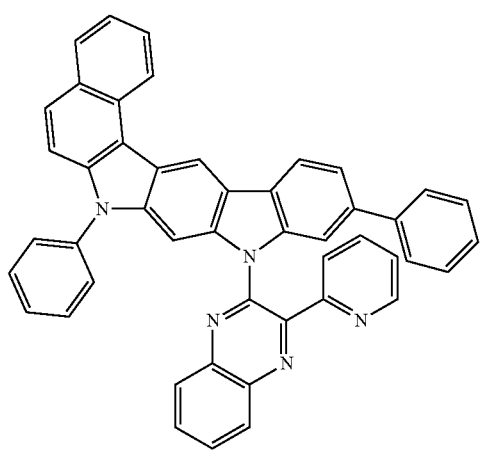
D-62
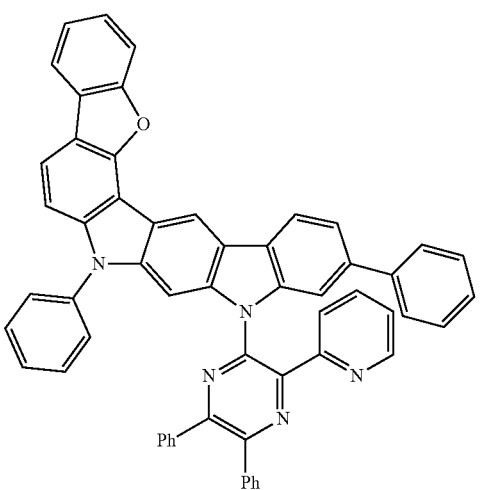

D-63
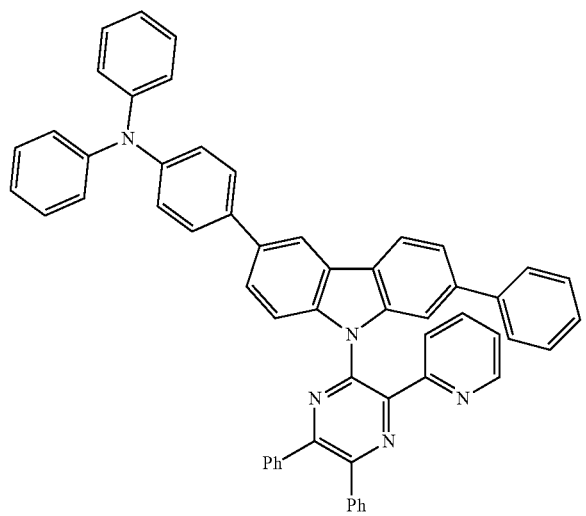
D-66
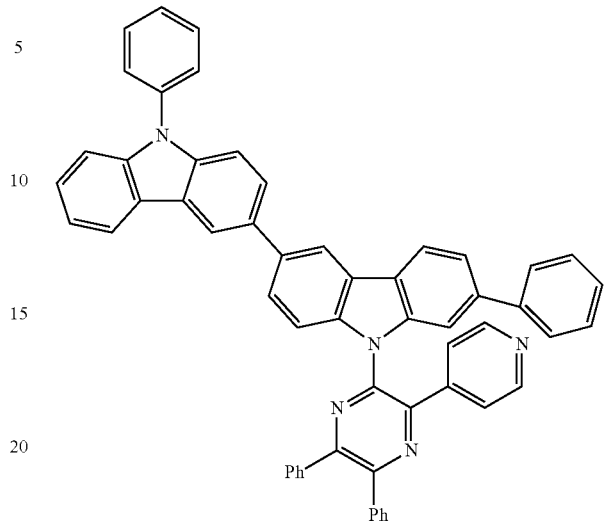
D-64
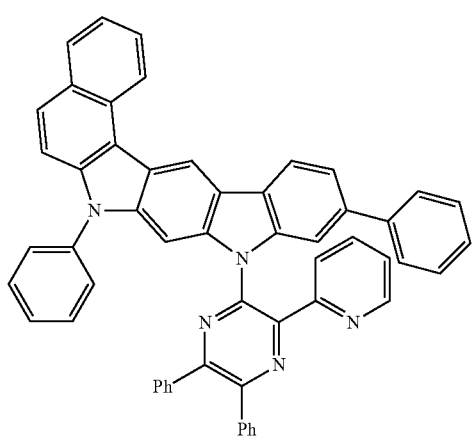
D-67
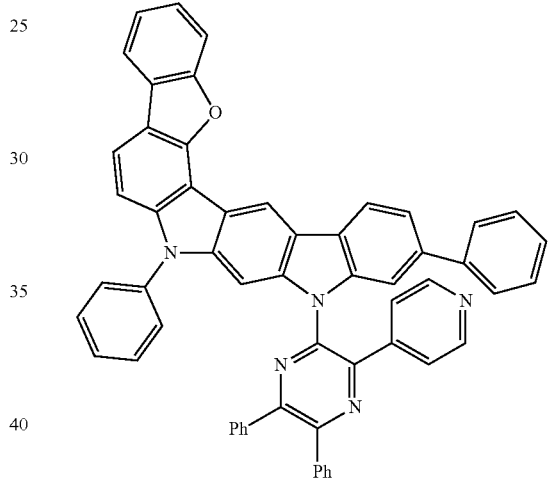
D-65
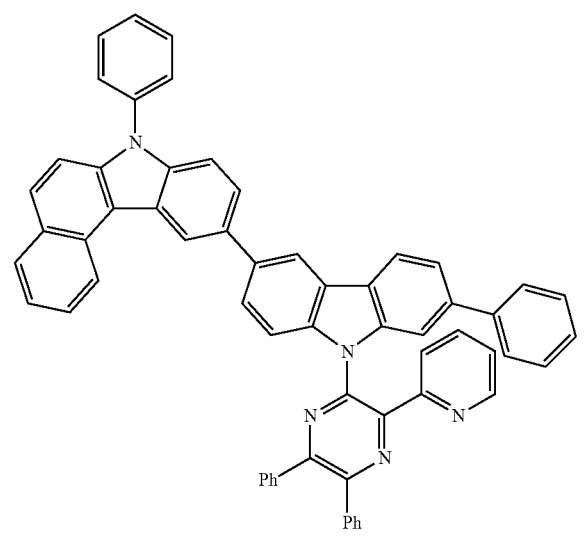
D-68
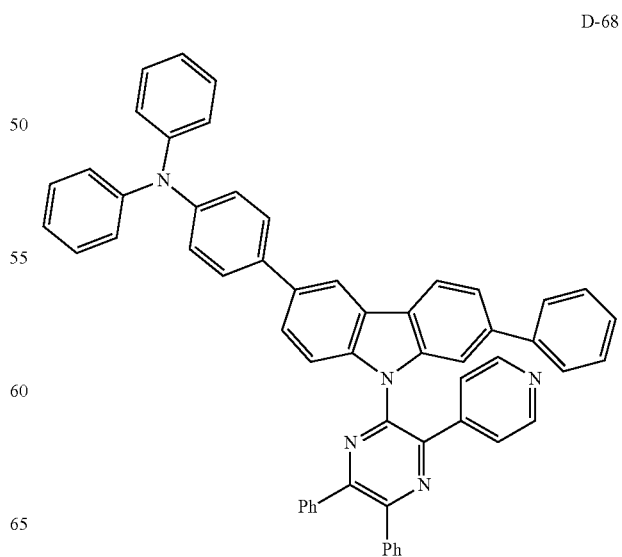

D-69
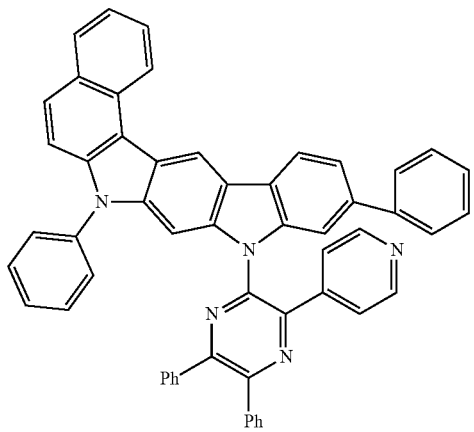
D-72
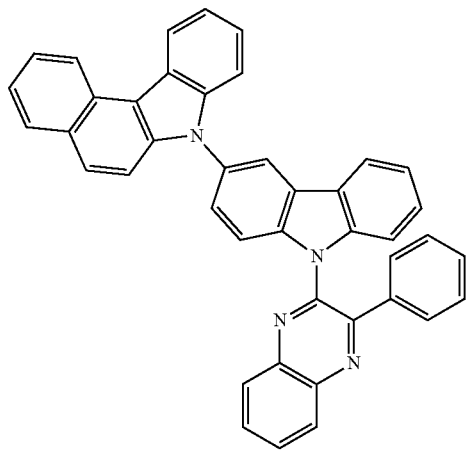
D-70
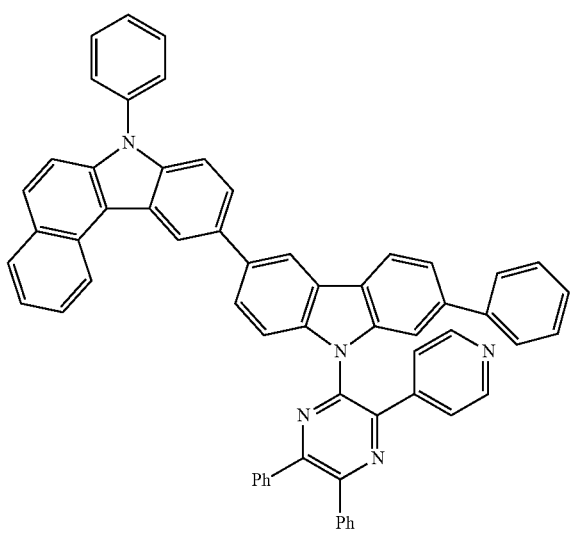
D-73
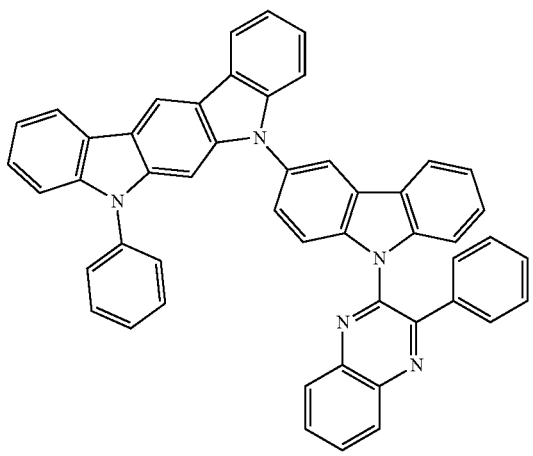
D-71
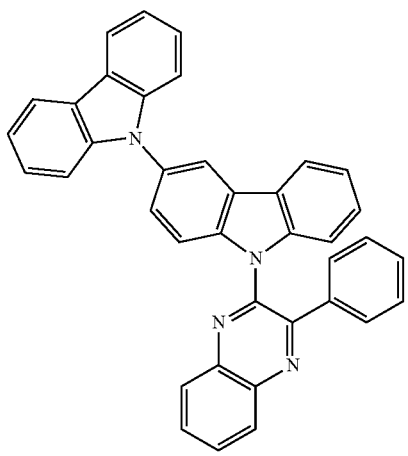
D-74
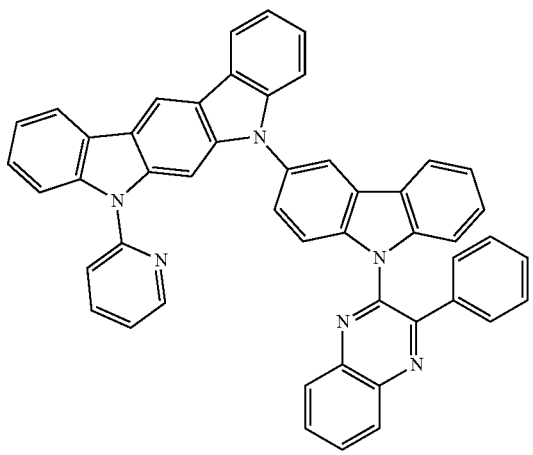

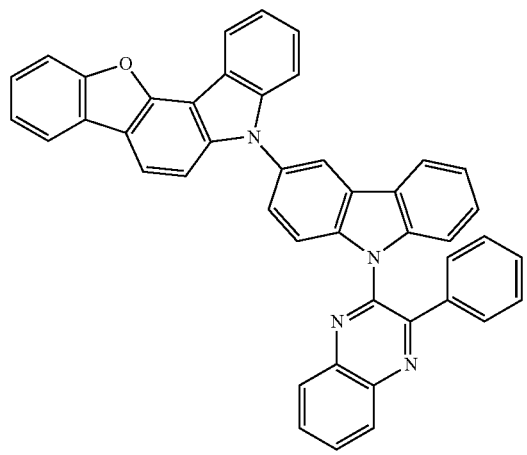

D-75

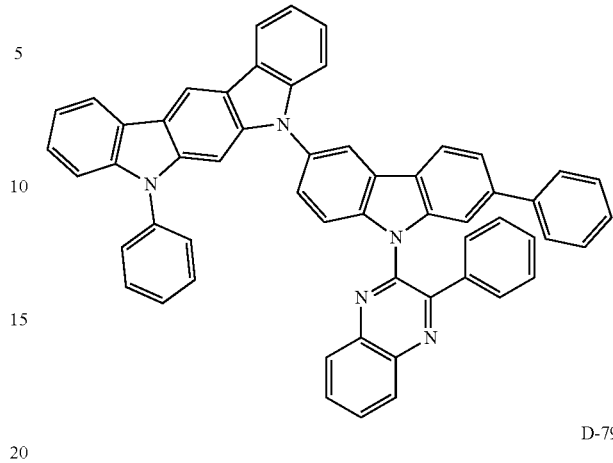

D-78

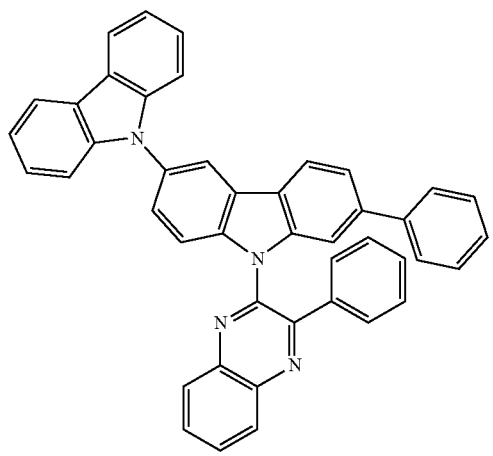

D-76

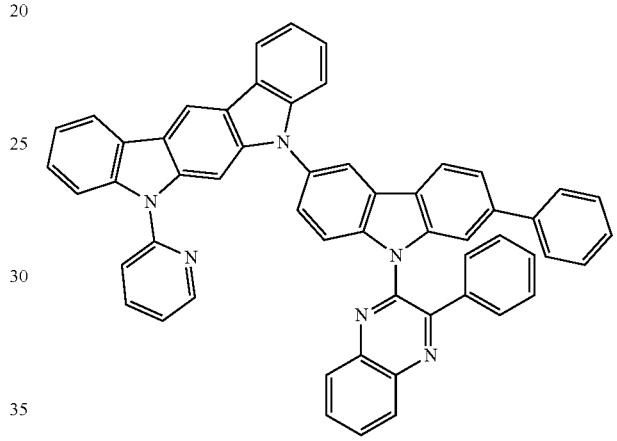

D-79

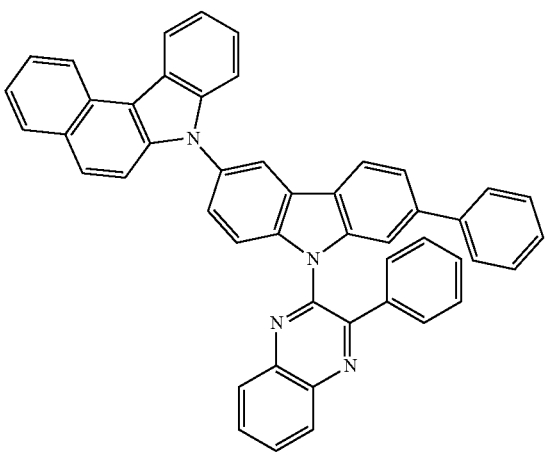

D-77

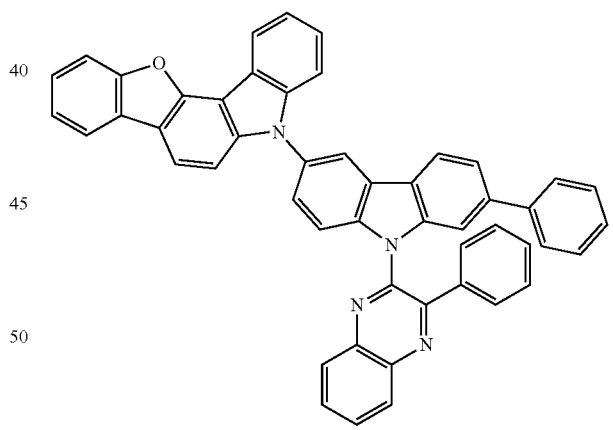

D-80

(wherein Ph represents a phenyl group.)

The compound of formula 1 can be prepared by a synthetic method known to a person skilled in the art. For example, it can be easily prepared using bromination, Suzuki reaction, Buchwald-Hartwig reaction, Ullmann reaction, etc.

The luminescent material for delayed fluorescence of the present invention may comprise one or two or more compounds represented by formula 1. In addition, the luminescent material for delayed fluorescence of the present invention can be in the form of a mixture or a composition. The luminescent material for delayed fluorescence of the present invention can be comprised of the compound of formula 1 alone, or can further include conventional materials generally used in organic electroluminescent materials and/or prior luminescent compound for delayed fluorescence.

The luminescent material for delayed fluorescence of the present invention shows thermally activated delayed fluorescence. Specifically, the luminescent material for delayed fluorescence of the present invention can be used for preparing a light-emitting layer of an organic electroluminescent device. In addition, the luminescent material for delayed fluorescence of the present invention can be preferably used as a dopant material in the light-emitting layer of an organic electroluminescent device.

In addition, according to another embodiment of the present invention, the present invention provides an organic electroluminescent device comprising the luminescent material for delayed fluorescence.

The organic electroluminescent device according to the present invention comprises a first electrode; a second electrode; and at least one organic layer between the first and second electrodes. The organic layer may comprise at least one light-emitting layer, and the light-emitting layer may comprise the luminescent material for delayed fluorescence of the present invention.

One of the first and second electrodes can be an anode, and the other can be a cathode. The organic layer comprises a light-emitting layer, and may further comprise at least one layer selected from the group consisting of a hole injection layer, a hole transport layer, an electron transport layer, an electron injection layer, an interlayer, a hole blocking layer, an electron blocking layer, and an electron buffer layer.

The organic electroluminescent device of the present invention may comprise the luminescent material for delayed fluorescence of the present invention in at least one of the light-emitting layer. The luminescent material for delayed fluorescence of the present invention may be used as a dopant material in the light-emitting layer.

The organic electroluminescent device of the present invention may comprise the luminescent material for delayed fluorescence of the present invention as a dopant material, and further comprise a host material. When the luminescent material for delayed fluorescence of the present invention and a host material are used together in the organic electroluminescent device of the present invention, the amount of the compound of formula 1 can be 0.1 wt % or higher, preferably 1 wt % or higher, and more preferably 5 wt % or higher, and 50 wt % or lower, and preferably 20 wt % or lower.

The host material can be preferably a compound of the following formula 8:

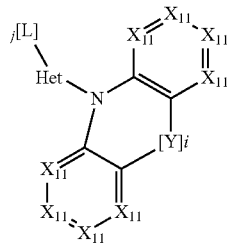

(8)

wherein $X_{11}$ independently represents N or $CR_{11}$;

$R_{11}$ independently represents hydrogen, deuterium, a substituted or unsubstituted (C1-C30)alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

Het represents a 5- to 30-membered heteroaryl(ene);

L represents hydrogen, a substituted or unsubstituted (C5-C30)aryl, or a substituted or unsubstituted 5- to 30-membered heteroaryl; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

Y is independently selected from a single bond, O, S, $NR_4$, $Si(R_4)_2$, $C(R_4)_2$, $PO(R_4)_2$, SO, $SO_2$, and $SeO_2$;

i represents an integer of 1 or 2;

$R_4$ represents a substituted or unsubstituted (C1-C30)alkyl, a substituted or unsubstituted (C5-C30)aryl, or a substituted or unsubstituted 5- to 30-membered heteroaryl; where there are two $R_4$'s, each of the two $R_4$'s may be the same or different, and the two $R_4$'s may be linked to each other to form a substituted or unsubstituted 11- to 60-membered polycyclic ring; and j represents an integer of 1 to 5; where j is an integer of 2 or more, each of L may be the same or different.

The compound of formula 8 can be preferably represented by the following formula 9:

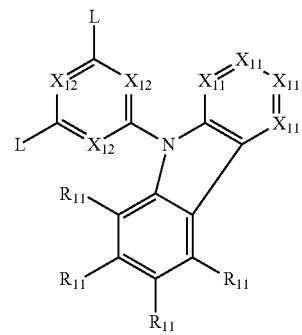

(9)

wherein $X_{11}$ independently represents N or $CR_{11}$;

$X_{12}$ independently represents N or $CR_{12}$;

$R_{11}$ and $R_{12}$ each independently represent hydrogen, deuterium, a substituted or unsubstituted (C1-C30)alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$; and L independently represents hydrogen, a substituted or unsubstituted (C5-C30)aryl, or a substituted or unsubstituted 5- to 30-membered heteroaryl; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$.

In formula 8 above, Het can be preferably a 5- to 30-membered nitrogen-containing heteroaryl(ene).

In formulas 8 and 9 above, $R_{11}$ and $R_{12}$ preferably each independently represent hydrogen, a substituted or unsubstituted phenyl, a substituted or unsubstituted biphenyl, a substituted or unsubstituted naphthyl, a substituted or unsubstituted pyrrolyl, a substituted or unsubstituted indolyl, a substituted or unsubstituted pyridyl, a substituted or unsubstituted carbazolyl, a substituted or unsubstituted benzofuranyl, a substituted or unsubstituted benzothiophenyl, a substituted or unsubstituted dibenzofuranyl, or a substituted or unsubstituted dibenzothiophenyl.

L preferably represents hydrogen, a substituted or unsubstituted phenyl, a substituted or unsubstituted indolyl, a substituted or unsubstituted carbazolyl, a substituted or unsubstituted carbolinyl, a substituted or unsubstituted benzofuranyl, a substituted or unsubstituted benzothiophenyl, a substituted or unsubstituted dibenzofuranyl, or a substituted or unsubstituted dibenzothiophenyl.

In formula 9 above, $X_{12}$ preferably independently represents N or CH; and more preferably, at least one $X_{12}$ is N.

The compound represented by formula 8 includes the following compounds, but is not limited thereto:

H-1
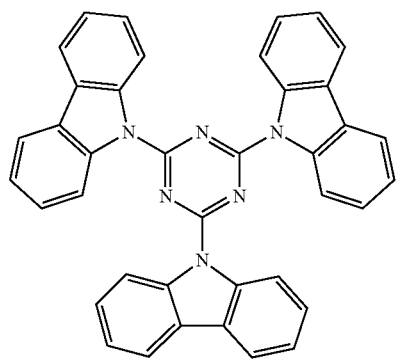

H-2
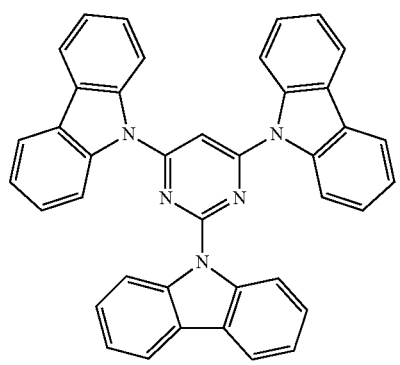

-continued

H-3
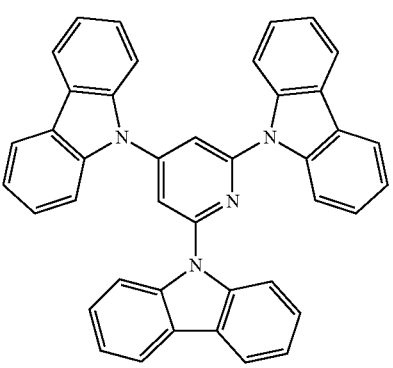

H-4
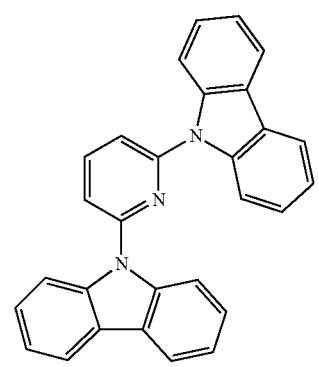

H-5
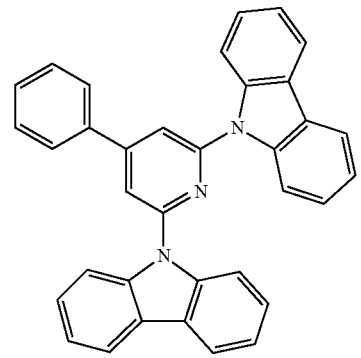

H-6
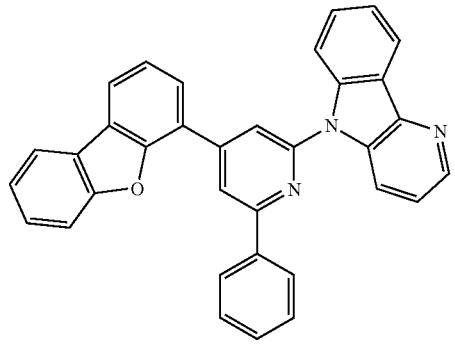

H-7
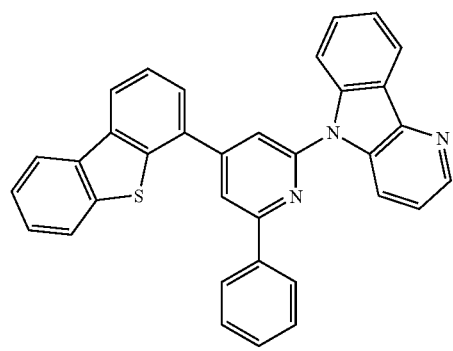
H-8
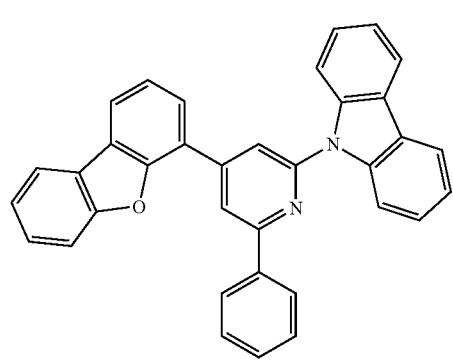
H-9
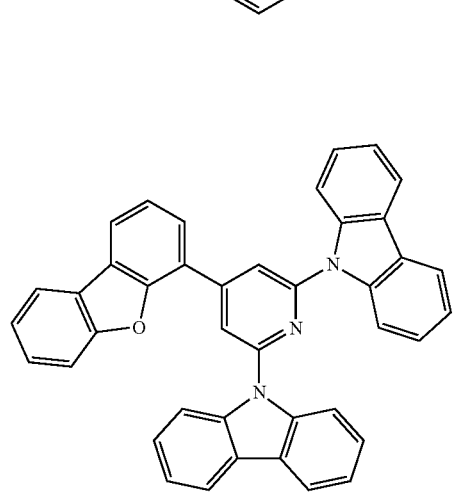
H-10
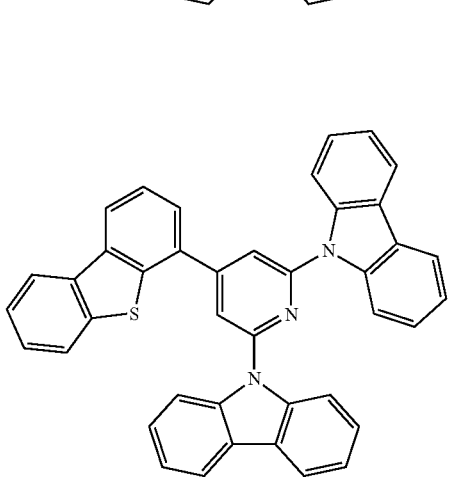
H-11
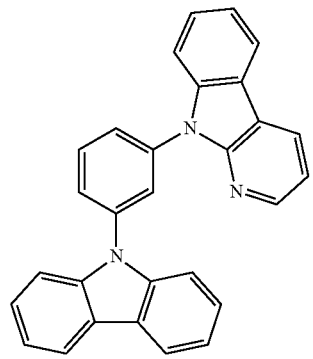
H-12
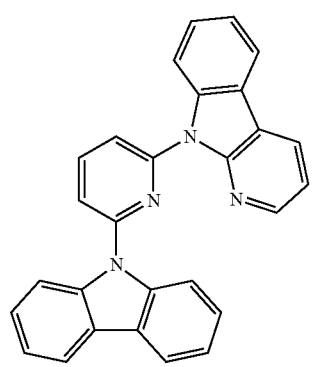
H-13
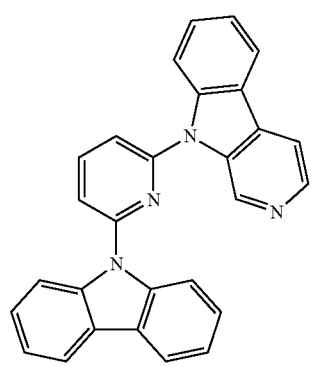
H-14
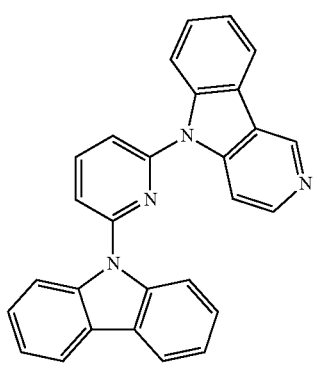

H-15
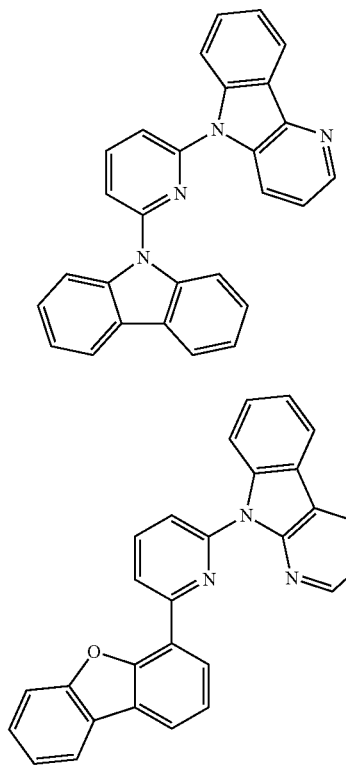
H-16
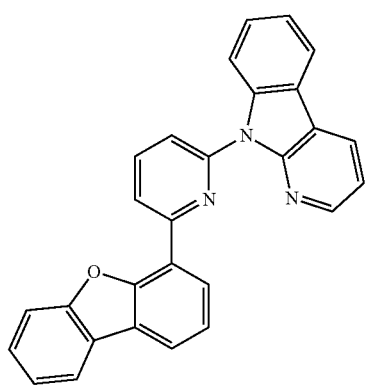
H-17
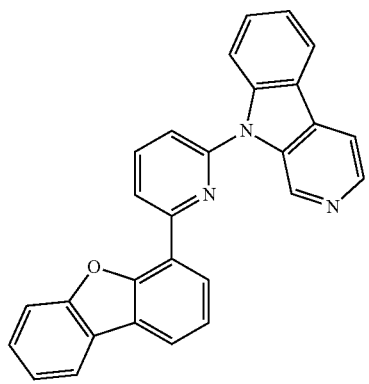
H-18
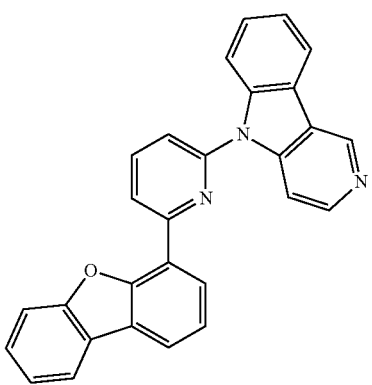
H-19
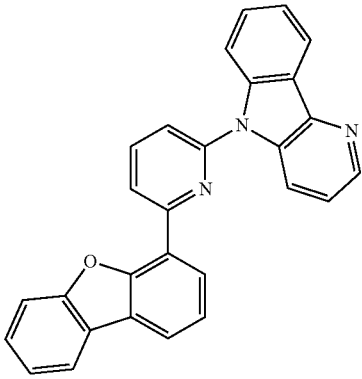
H-20
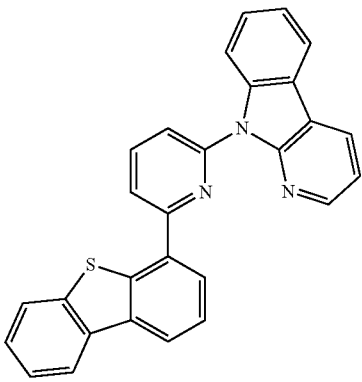
H-21
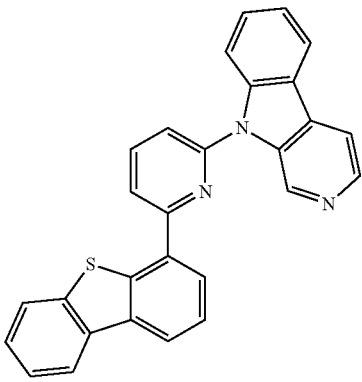
H-22
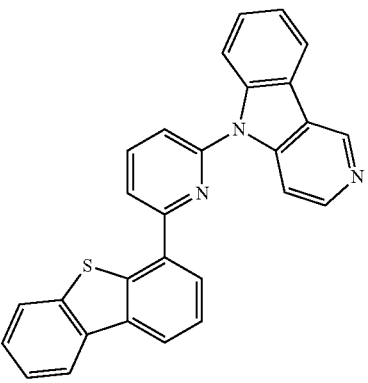

H-23 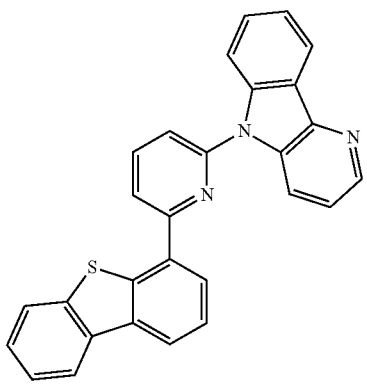

H-24 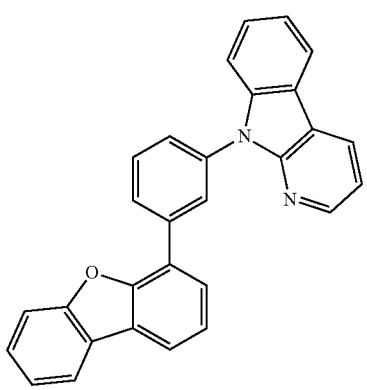

H-25 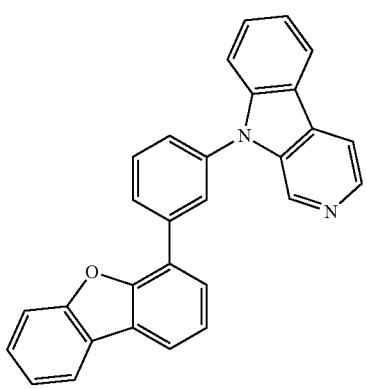

H-26 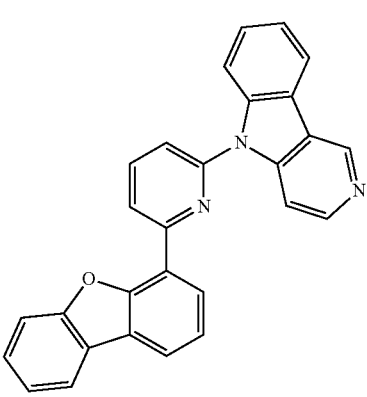

H-27 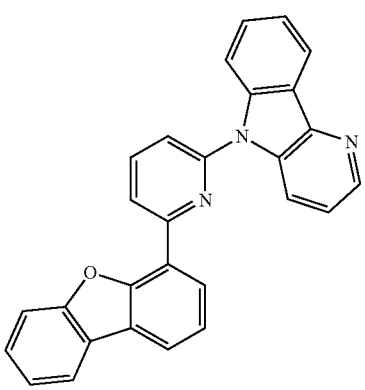

The organic electroluminescent device according to the present invention may further comprise at least one compound selected from the group consisting of arylamine-based compounds and styrylarylamine-based compounds.

In addition, in the organic electroluminescent device according to the present invention, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

In addition, the organic electroluminescent device according to the present invention may emit white light by further comprising at least one light-emitting layer which comprises a blue electroluminescent compound, a red electroluminescent compound, or a green electroluminescent compound known in the field, besides the light-emitting layer comprising the compound of the present invention. Also, if necessary, a yellow or orange light-emitting layer can be comprised in the device.

In the organic electroluminescent device of the present invention, at least one layer (hereinafter, "a surface layer") is preferably placed on an inner surface(s) of one or both electrodes selected from a chalcogenide layer, a metal halide layer and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x(1 \leq X \leq 2)$, $AlO_x$ $(1 \leq X \leq 1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

In the organic electroluminescent device according to the present invention, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an electroluminescent device having two or more electroluminescent layers and emitting white light.

In order to form each layer of the organic electroluminescent device of the present invention, dry film-forming methods such as vacuum evaporation, sputtering, plasma, and ion plating methods, or wet film-forming methods such as ink jet printing, nozzle printing, slot coating, spin coating, dip coating, and flow coating methods can be used.

When using a wet film-forming method, a thin film is formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the luminescent properties of the compound of the present invention will be explained in detail with reference to the following examples.

Example 1: Preparation of an OLED Device Using the Luminescent Material for Delayed Fluorescence According to the Present Invention An OLED device was produced using the luminescent material of the present invention. A transparent electrode indium tin oxide (ITO) thin film (15 Ω/sq) on a glass substrate for an organic light-emitting diode (OLED) device was subjected to an ultrasonic washing with trichloroethylene, acetone, ethanol, and distilled water, sequentially, and then was stored in isopropanol. The ITO substrate was then mounted on a substrate holder of a vacuum vapor depositing apparatus. HIL-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby evaporating HIL-1 of 60 nm thickness on the ITO substrate. Next, HIL-2 was introduced into another cell of said vacuum vapor depositing apparatus, and was evaporated to have a thickness of 5 nm by applying an electric current to the cell. HTL-1 was deposited to have a thickness of 15 nm, HTL-2 was deposited to have a thickness of 5 nm on HTL-1, and H-11 was further deposited to have a thickness of 5 nm as an electron blocking layer. A light-emitting layer was deposited as follows. H-2 was introduced into one cell of said vacuum vapor depositing apparatus as a host, and compound D-2 was introduced into another cell as a thermally activated delayed fluorescence (TADF) dopant of the present invention. The two materials were evaporated at different rates, so that the dopant was deposited in a doping amount of 15 wt % based on the total amount of the host and dopant to deposit a light-emitting layer having a thickness of 400 nm. ETL-1 was evaporated at another vacuum vapor depositing apparatus to have a thickness of 5 nm on the light-emitting layer, and ETL-2 and lithium quinolate were then introduced into another two cells, evaporated at the doping rate of 30 to 70 wt %, and deposited to have a thickness of 30 nm. Next, after depositing lithium quinolate as an electron injection layer having a thickness of 2 nm, an Al cathode having a thickness of 150 nm was deposited by another vacuum vapor deposition apparatus. Thus, an OLED device was produced. All the materials were those purified by vacuum sublimation at $10^{-6}$ torr. As a result, an efficiency of 38.8 cd/A at 1000 nit was shown, and the CIE color coordinate was 0.345, 0.581.

Meanwhile, a photoluminescence spectrum of compound D-2 used in Example 1 at room temperature and 77K was evaluated and illustrated in FIG. 1. From the spectrum, the energy of the singlet exciton state and the energy of the triplet exciton state were obtained, and it was determined that the $\Delta E_{ST}$ of compound D-2 is 0.03 eV. By this low $\Delta E_{ST}$, it is interpreted that the triplet exciton is subjected to reverse-intersystem crossing to a singlet exciton and emits light, i.e. delayed fluorescence.

Figure 2:
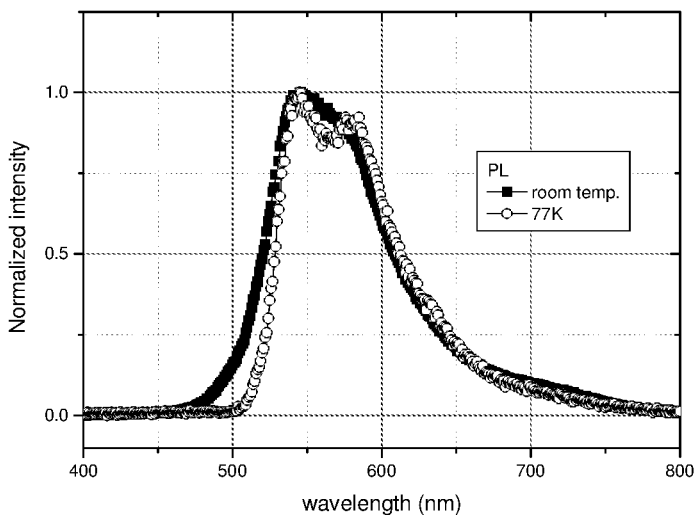
FIG. 2 illustrates a photoluminescence spectrum at low temperature of compound D-1 of Example 2.

Example 2: Preparation of an OLED Device Using the Luminescent Material for Delayed Fluorescence According to the Present Invention An OLED device was produced in the same manner as in Example 1, except for using compound H-2 as a host and compound D-1 as a dopant of the luminescent material. As a result, an efficiency of 38.8 cd/A at 1000 nit was shown, and the CIE color coordinate was 0.334, 0.558. It is verified that the device using the organic electroluminescent compound of the present invention as a TADF dopant material has excellent current and luminous efficiencies. The photoluminescence spectrum of compound D-1 was measured in the same manner as in Example 1 and illustrated in FIG. 2. From FIG. 2, it was determined that the $\Delta E_{ST}$ of compound D-1 is 0.08 eV, and thus compound D-1 emits light by delayed fluorescence.

Figure 3:
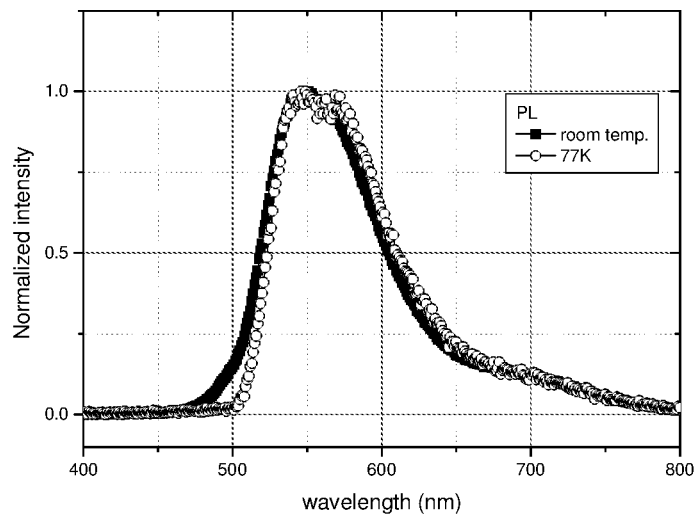
FIG. 3 illustrates a photoluminescence spectrum at low temperature of compound D-73 of Example 3.

Example 3: Preparation of an OLED Device Using the Luminescent Material for Delayed Fluorescence According to the Present Invention An OLED device was produced in the same manner as in Example 1, except for using compound H-2 as a host and compound D-73 as a dopant of the luminescent material. As a result, an efficiency of 25.0 cd/A at 1000 nit was shown, and the CIE color coordinate was 0.332, 0.561. It is verified that the device using the organic electroluminescent compound of the present invention as a TADF dopant material has excellent current and luminous efficiencies. The photoluminescence spectrum of compound D-73 was measured in the same manner as in Example 1 and illustrated in FIG. 3. From FIG. 3, it was determined that the $\Delta E_{ST}$ of compound D-73 is 0.03 eV, and thus compound D-73 emits light by delayed fluorescence.

Figure 4:
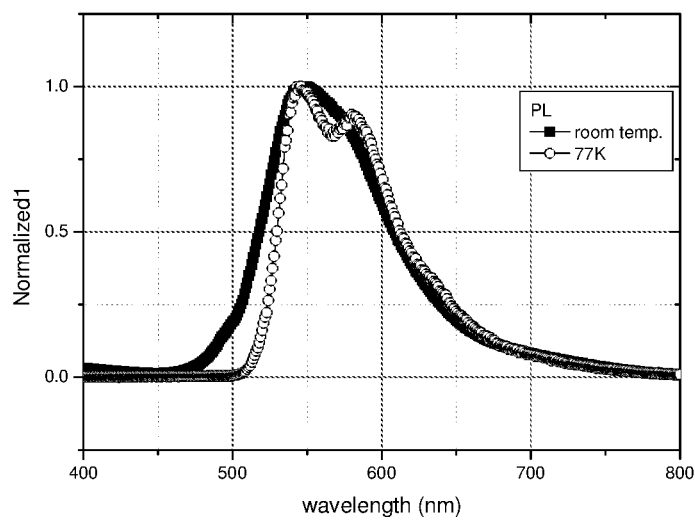
FIG. 4 illustrates a photoluminescence spectrum at low temperature of compound D-41 of Example 4.

Example 4: Preparation of an OLED Device Using the Luminescent Material for Delayed Fluorescence According to the Present Invention An OLED device was produced in the same manner as in Example 1, except for using compound H-2 as a host and compound D-41 as a dopant of the luminescent material. As a result, an efficiency of 24.4 cd/A at 1000 nit was shown, and the CIE color coordinate was 0.336, 0.557. It is verified that the device using the organic electroluminescent compound of the present invention as a TADF dopant material has excellent current and luminous efficiencies. The photoluminescence spectrum of compound D-41 was measured in the same manner as in Example 1 and illustrated in FIG. 4. From FIG. 4, it was determined that the $\Delta E_{ST}$ of compound D-41 is 0.07 eV, and thus compound D-41 emits light by delayed fluorescence.

Figure 5:
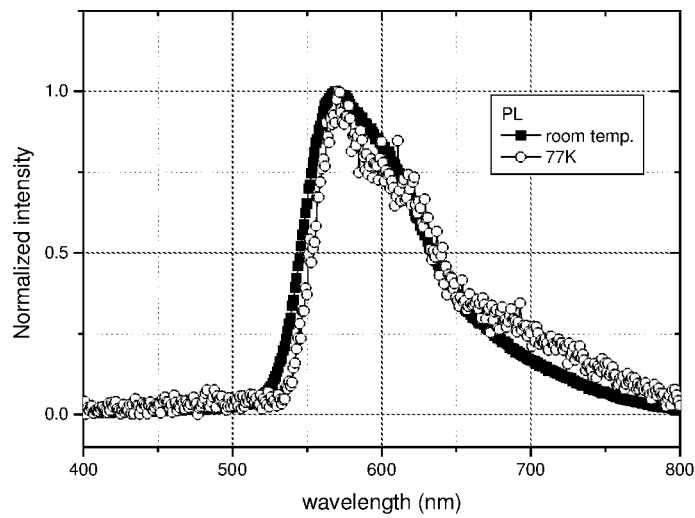
FIG. 5 illustrates a photoluminescence spectrum at low temperature of compound D-4 of Example 5.

Example 5: Preparation of an OLED Device Using the Luminescent Material for Delayed Fluorescence According to the Present Invention An OLED device was produced in the same manner as in Example 1, except for using compound H-2 as a host and compound D-4 as a dopant of the luminescent material. As a result, an efficiency of 24.2 cd/A at 1000 nit was shown, and the CIE color coordinate was 0.427, 0.552. It is verified that the device using the organic electroluminescent compound of the present invention as a TADF dopant material has excellent current and luminous efficiencies. The photoluminescence spectrum of compound D-4 was measured in the same manner as in Example 1 and illustrated in FIG. 5. From FIG. 5, it was determined that the $\Delta E_{ST}$ of compound D-4 is 0.04 eV, and thus compound D-4 emits light by delayed fluorescence.

Figure 6:
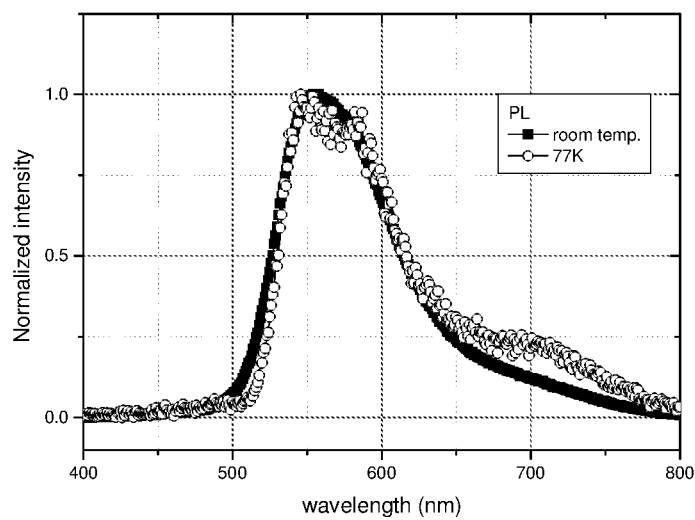
FIG. 6 illustrates a photoluminescence spectrum at low temperature of compound D-3 of Example 6.

Example 6: Preparation of an OLED Device Using the Luminescent Material for Delayed Fluorescence According to the Present Invention An OLED device was produced in the same manner as in Example 1, except for using compound H-2 as a host and compound D-3 as a dopant of the luminescent material. As a result, an efficiency of 23.5 cd/A at 1000 nit was shown, and the CIE color coordinate was 0.384, 0.552. It is verified that the device using the organic electroluminescent compound of the present invention as a TADF dopant material has excellent current and luminous efficiencies. The photoluminescence spectrum of compound D-3 was measured in the same manner as in Example 1 and illustrated in FIG. 6. From FIG. 6, it was determined that the $\Delta E_{ST}$ of compound D-3 is 0.05 eV, and thus compound D-3 emits light by delayed fluorescence.

Figure 7:
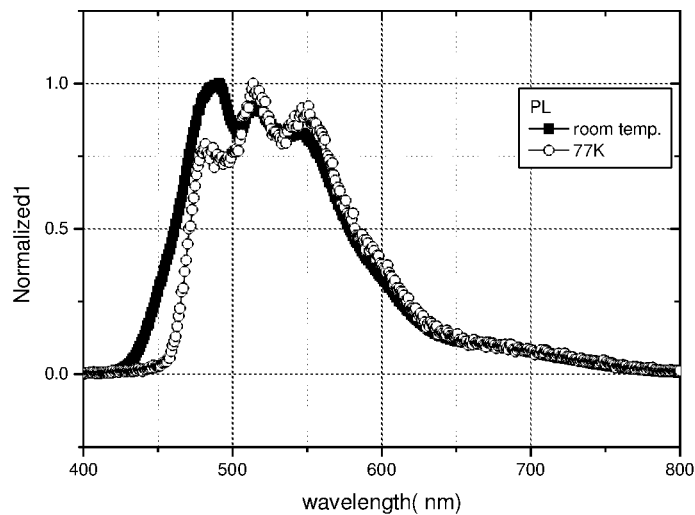
FIG. 7 illustrates a photoluminescence spectrum at low temperature of compound D-5 of Example 7.

Example 7: Preparation of an OLED Device Using the Luminescent Material for Delayed Fluorescence According to the Present Invention An OLED device was produced in the same manner as in Example 1, except for using compound H-2 as a host and compound D-5 as a dopant of the luminescent material. As a result, an efficiency of 22.4 cd/A at 1000 nit was shown, and the CIE color coordinate was 0.402, 0.559. It is verified that the device using the organic electroluminescent compound of the present invention as a TADF dopant material has excellent current and luminous efficiencies. The photoluminescence spectrum of compound D-5 was measured in the same manner as in Example 1 and illustrated in FIG. 7. From FIG. 7, it was determined that the $\Delta E_{ST}$ of compound D-5 is 0.06 eV, and thus compound D-5 emits light by delayed fluorescence.

Figure 8:
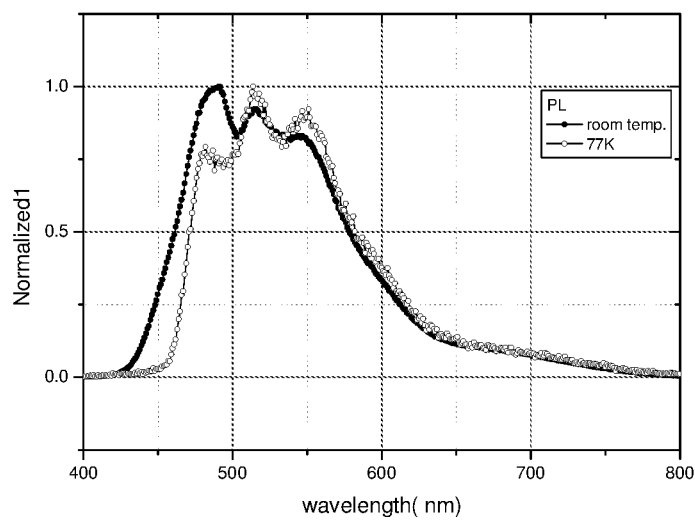
FIG. 8 illustrates a photoluminescence spectrum at low temperature of compound CD-2 of Comparative Example 1.

Comparative Example 1: Luminous Properties of the OLED Device Using Conventional Luminescent Material for Delayed Fluorescence An OLED device was produced in the same manner as in Example 1, except for using compound H-2 as a host and compound CD-2 as below as a dopant of the luminescent material. As a result, an efficiency of 15.9 cd/A at 1000 nit was shown, and the CIE color coordinate was 0.279, 0.463. It is verified that the device using the organic electroluminescent compound of the present invention as a TADF dopant material has superior current and luminous efficiencies to that using the comparative compound. The photoluminescence spectrum of compound CD-2 was measured in the same manner as in Example 1 and illustrated in FIG. 8. From FIG. 8, it was determined that the $\Delta E_{ST}$ of compound CD-2 is 0.12 eV, and thus compound CD-2 emits light by delayed fluorescence.

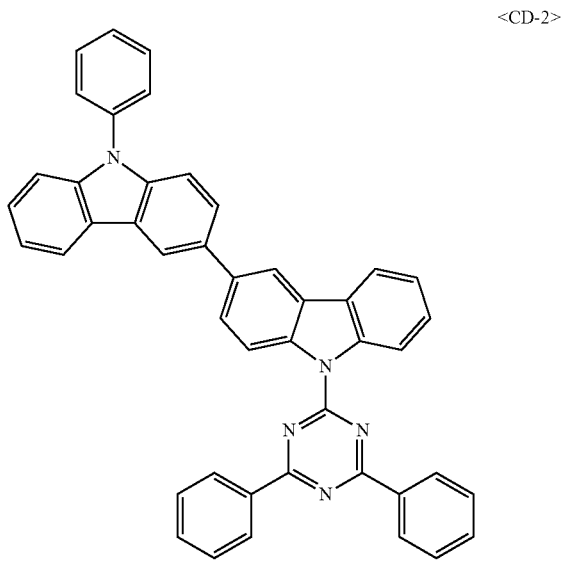

<CD-2>

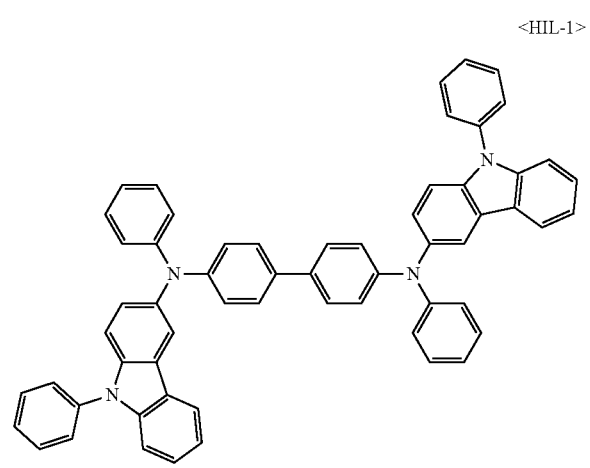

<HIL-1>

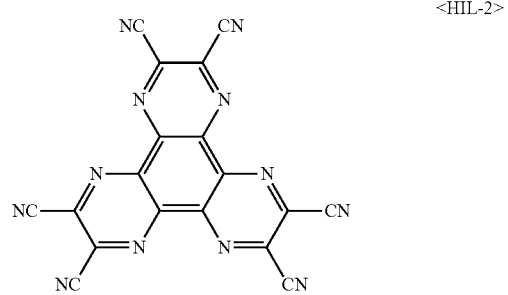

<HIL-2>

-continued

<HTL-1>
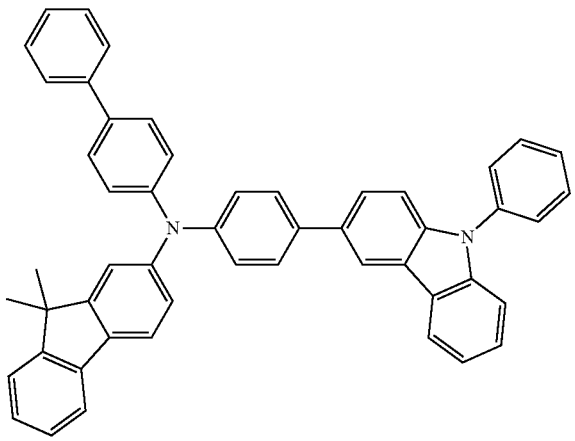

<HTL-2>
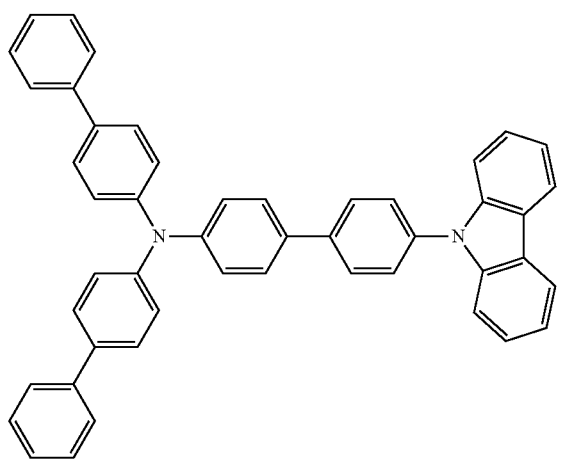

<H-11>
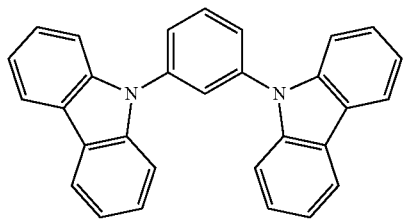

<H-2>
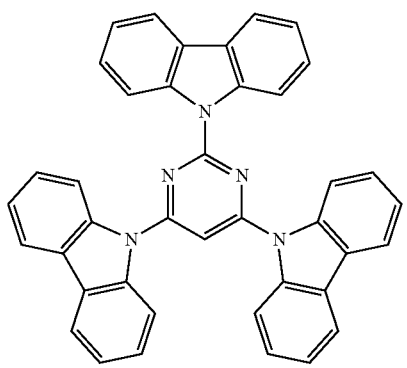

-continued

<ETL-1>
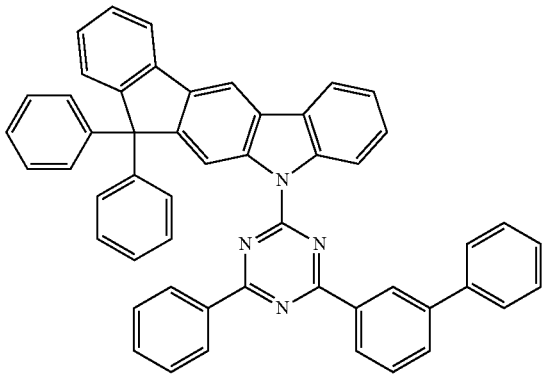

<ETL-2>
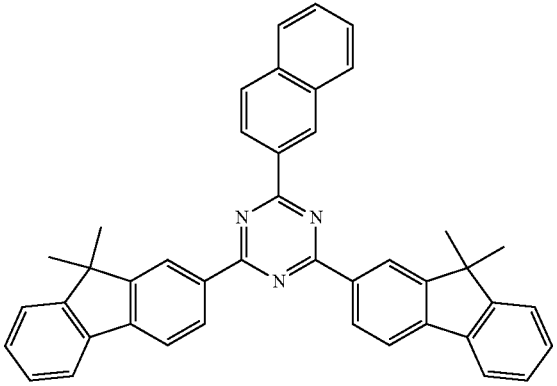

The invention claimed is:

1. An organic electroluminescent device comprising a luminescent material for delayed fluorescence comprising a compound of the following formula 1 as a dopant material, and further comprising a compound of the following formula 8 as a host material:

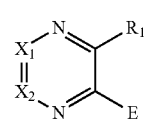

(1)

wherein $R_1$ represents a substituted or unsubstituted (C1-C30) alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

$X_1$ represents —$CR_3$ or N;
$X_2$ represents —$CR_6$ or N;
$R_3$ and $R_6$ each independently represent hydrogen, deuterium, a substituted or unsubstituted (C1-C30)alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, SO$_2$, and SeO$_2$;
E is represented by the following formulae 2-1 to 2-5, 2-9 to 2-13, 2-15, 2-19 to 2-28, 2-30, and 2-32 to 2-35;
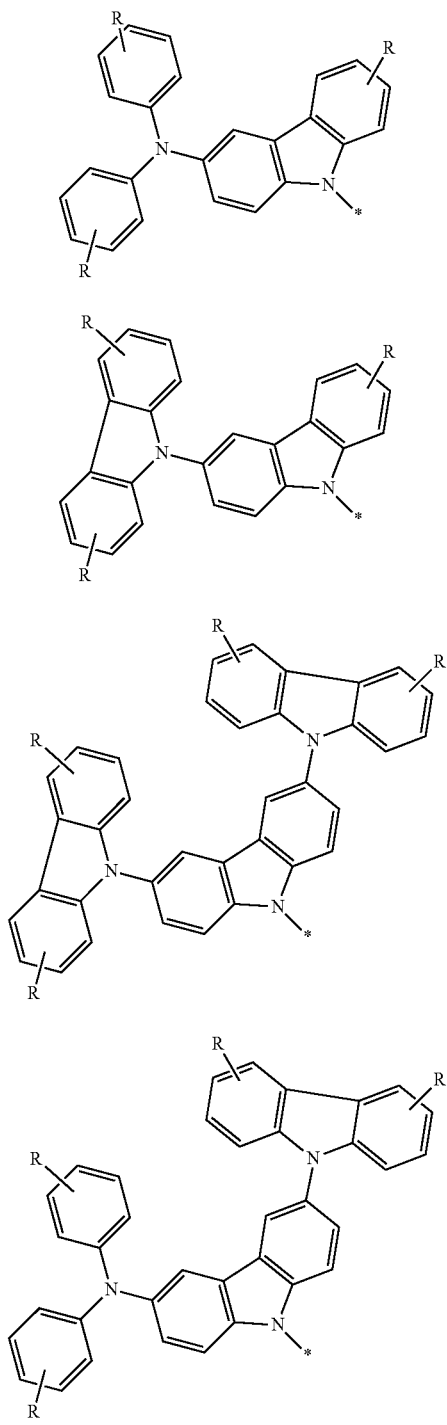
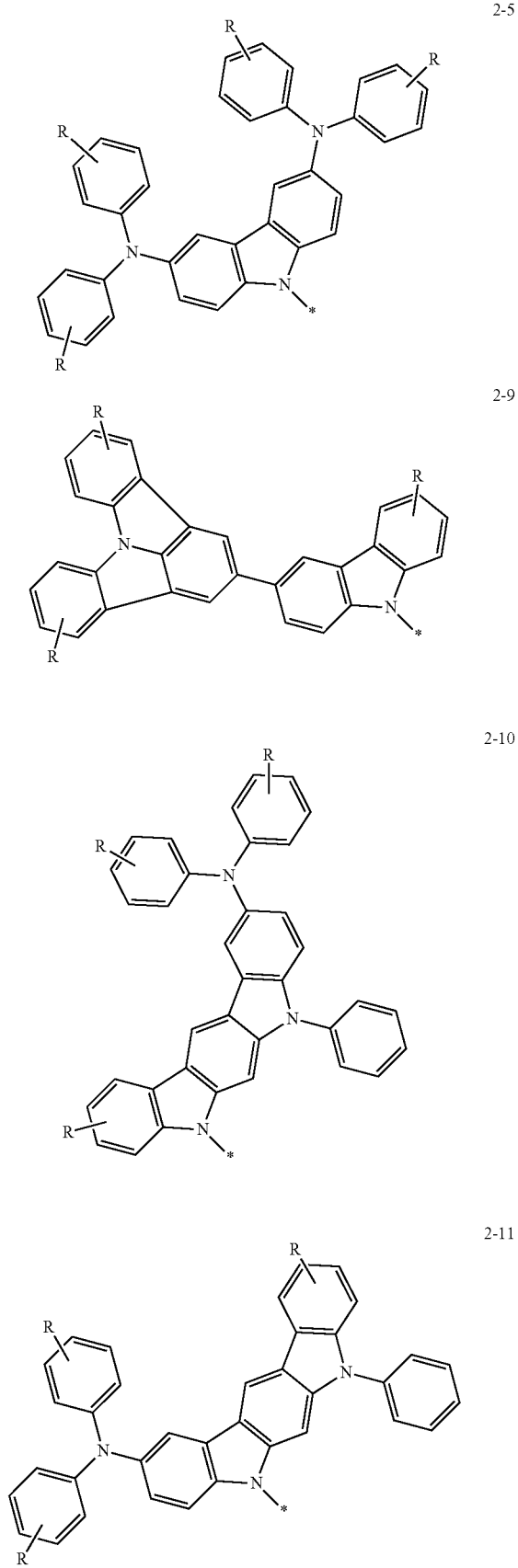

-continued
2-12
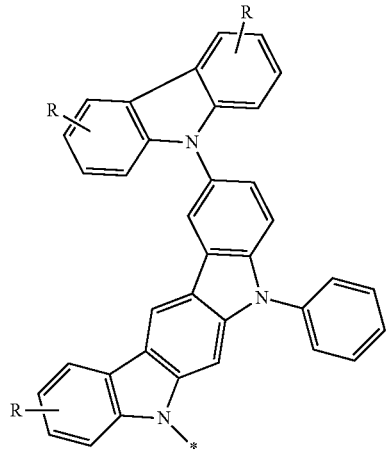
2-13
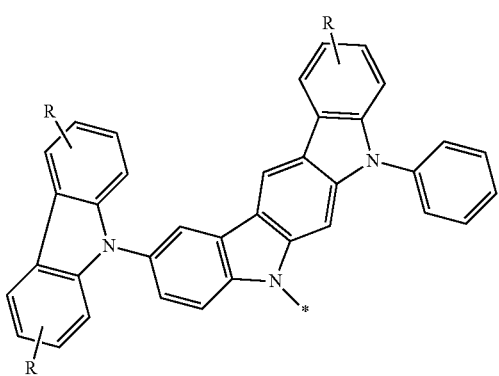
2-15
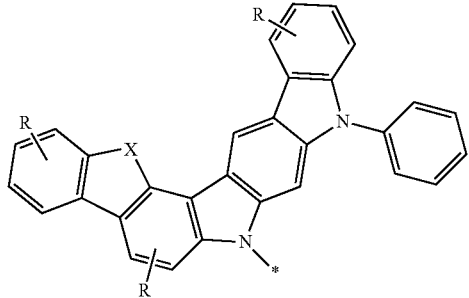
2-19
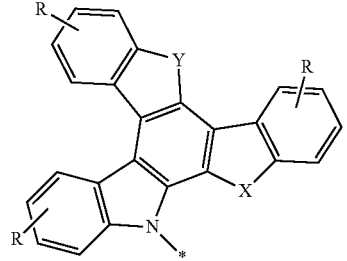
-continued
2-20
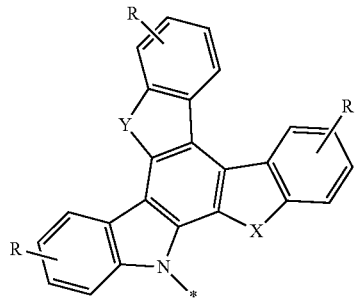
2-21
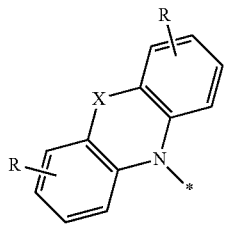
2-22
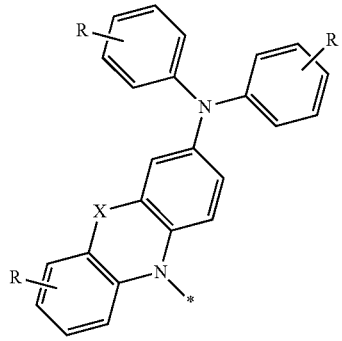
2-23
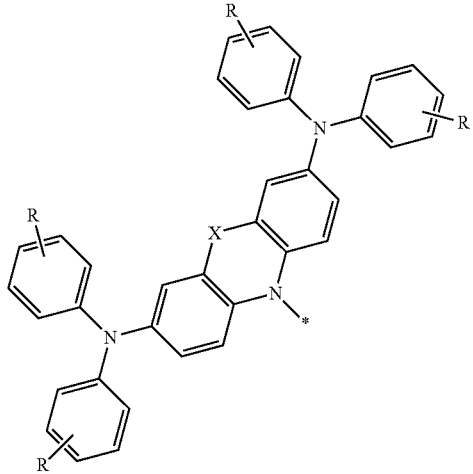

-continued
2-24
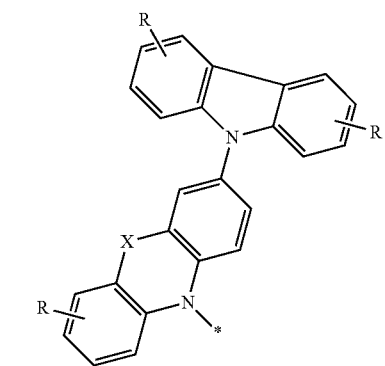
2-25
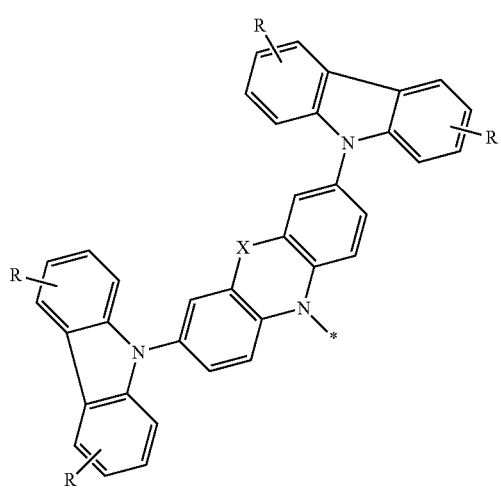
2-26
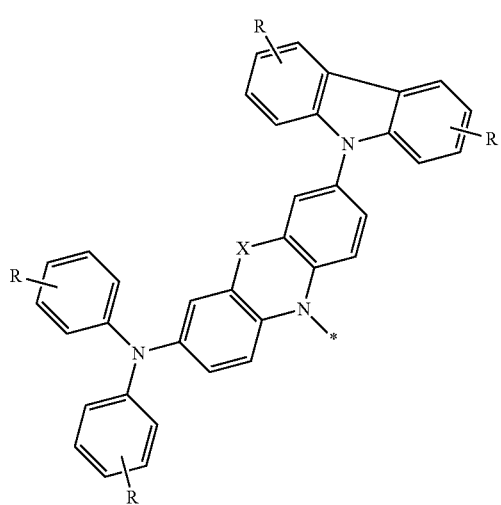
-continued
2-27
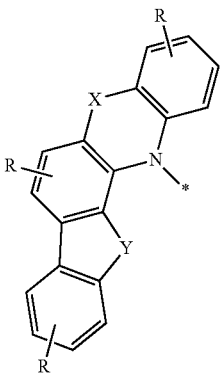
2-28
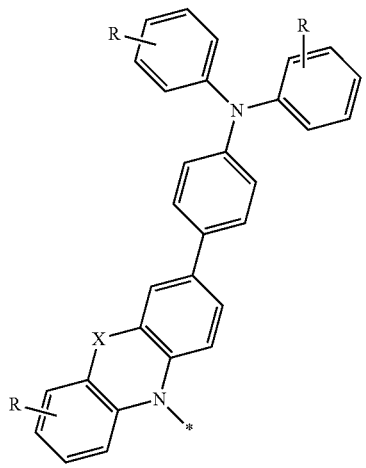
2-30
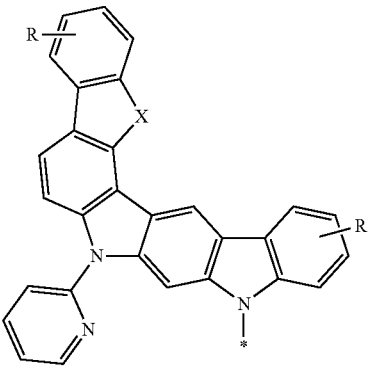
2-30
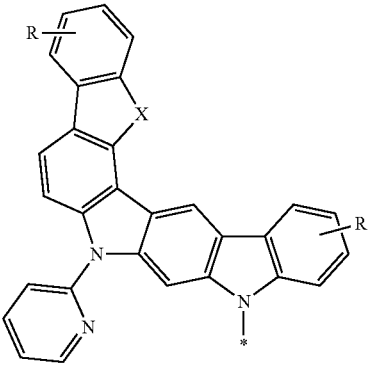

-continued 2-32

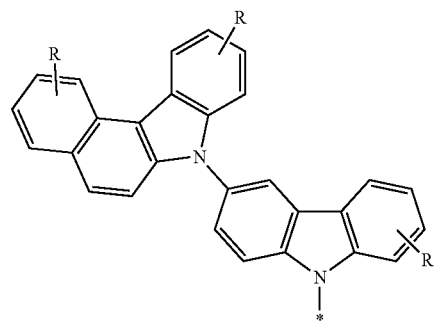

2-33

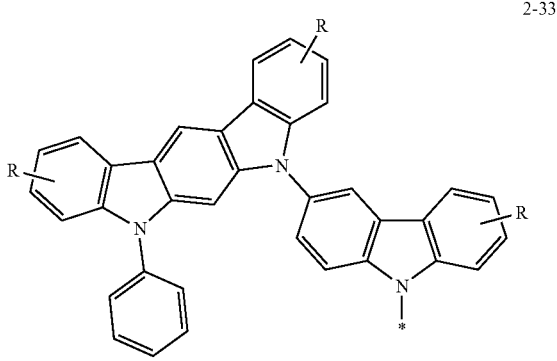

2-34

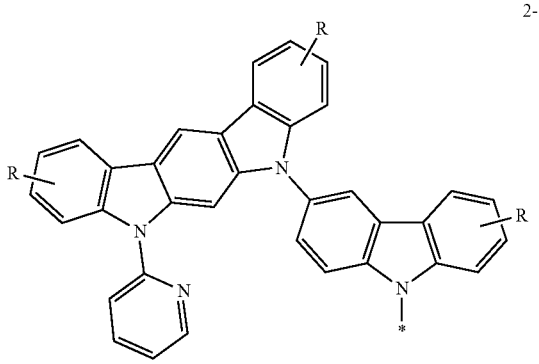

2-35

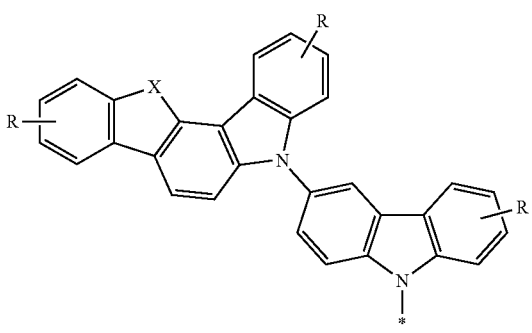

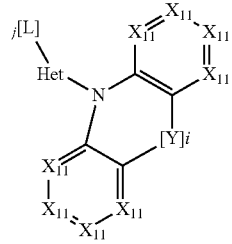

(8)

wherein

X and Y each independently are selected from O, S, $NR_4$, $Si(R_4)_2$, $C(R_4)_2$, $PO(R_4)_2$, SO, $SO_2$, and $SeO_2$;

$R_4$ represents a substituted or unsubstituted (C1-C30) alkyl, a substituted or unsubstituted (C5-C30)aryl, or a substituted or unsubstituted 5- to 30-membered heteroaryl; where there are two $R_4$'s, each of the two $R_4$'s may be the same or different, and the two $R_4$'s may be linked to each other to form a substituted or unsubstituted 11- to 60-membered polycyclic ring; and R each independently represents hydrogen, a substituted or unsubstituted (C1-C30)alkyl, a substituted or unsubstituted (C5-C30)aryl, or a substituted or unsubstituted 5- to 30-membered heteroaryl; and

* represents a bonding site between the ring comprising $X_1$ and $X_2$, and E;

independently represents N or $CR_{11}$;

$R_{11}$ independently represents hydrogen, deuterium, a substituted or unsubstituted (C1-C30)alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

Het represents a 5- to 30-membered heteroaryl(ene);

L represents hydrogen, a substituted or unsubstituted (C5-C30)aryl, or a substituted or unsubstituted 5- to 30-membered heteroaryl; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$;

i represents an integer of 1 or 2; and j represents an integer of 1 to 5; where j is an integer of 2 or more, each of L may be the same or different.

2. The organic electroluminescent device comprising the luminescent material for delayed fluorescence according to claim 1, wherein formula 1 is selected from the following formulas 1-1 to 1-16:

1-1

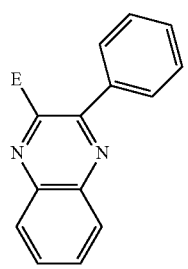

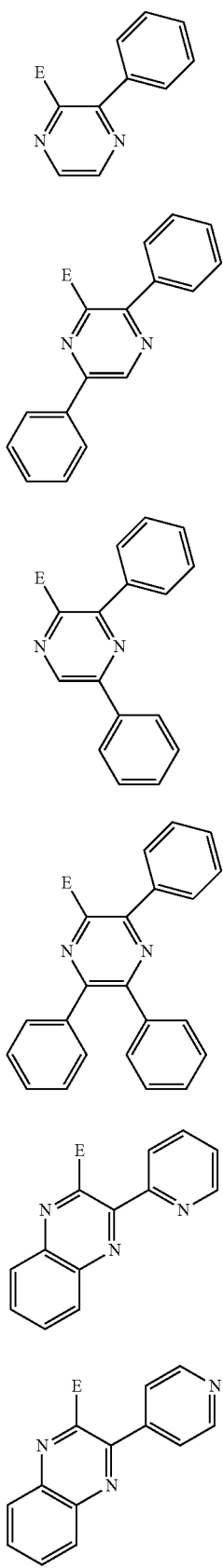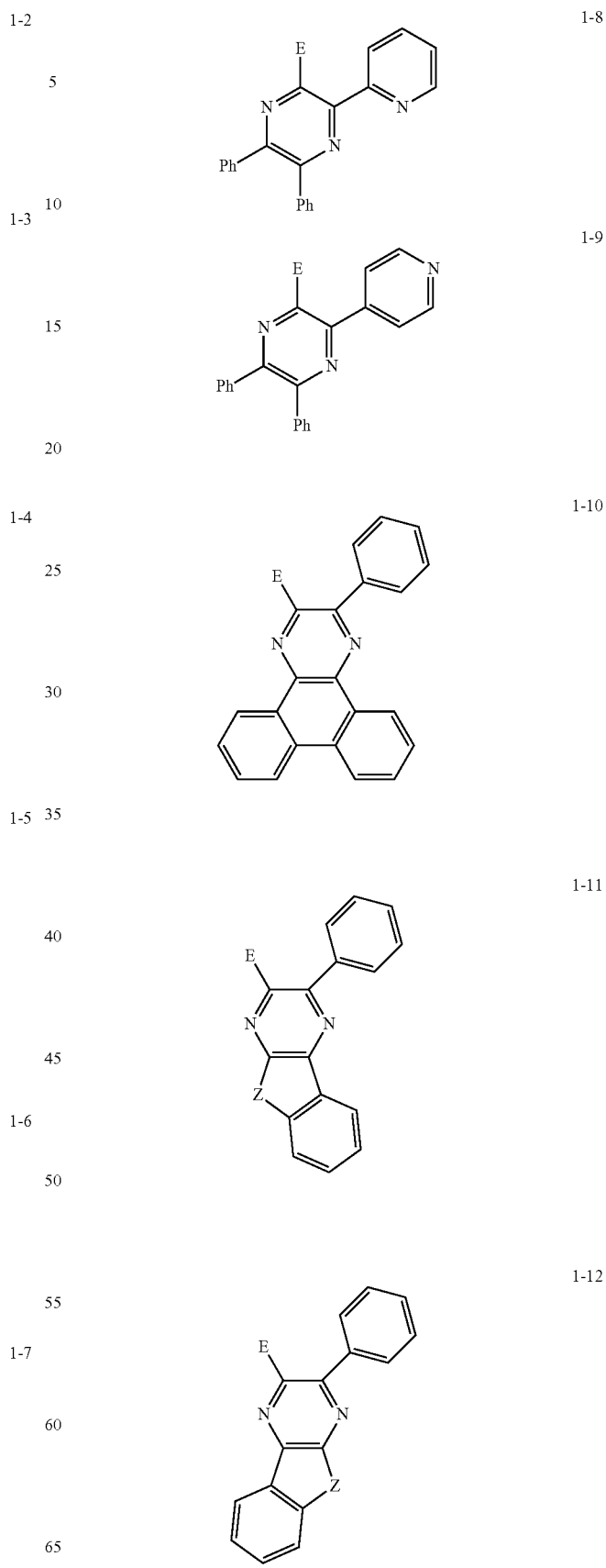

-continued 1-13
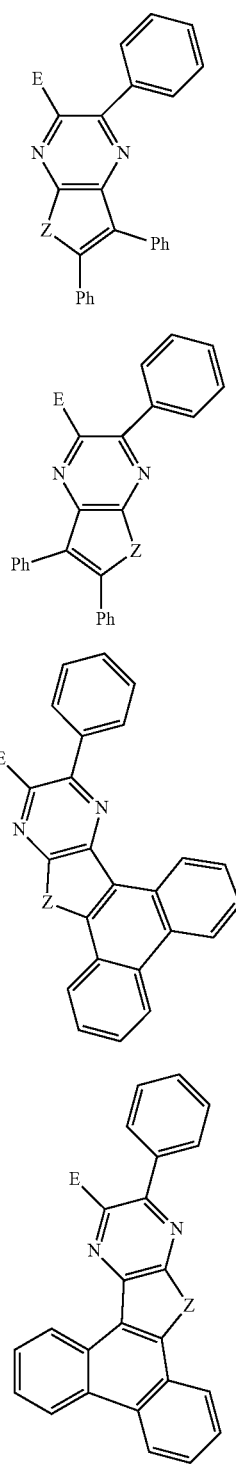

1-14

1-15

1-16 wherein

Z is selected from O, S, $NR_8$, $Si(R_8)_2$, $C(R_8)_2$, $PO(R_8)_2$, SO, $SO_2$, and $SeO_2$;

$R_8$ represents a substituted or unsubstituted (C1-C30) alkyl, a substituted or unsubstituted (C5-C30)aryl, or a substituted or unsubstituted 5- to 30-membered heteroaryl; and Ph represents phenyl, and E is as defined in claim 1.

3. The organic electroluminescent device comprising the luminescent material for delayed fluorescence according to claim 1, wherein the compound represented by formula 1 is selected from the group consisting of:

D-11
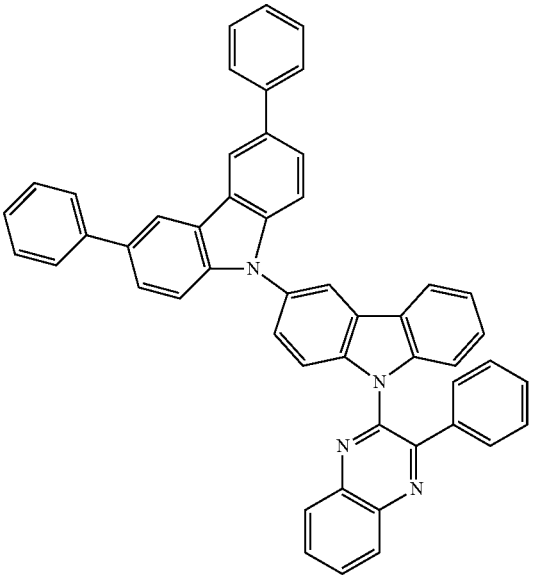

D-31
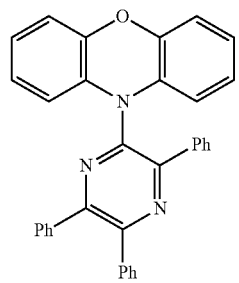

D-32
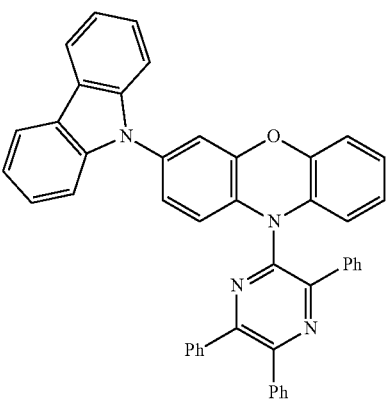

D-33
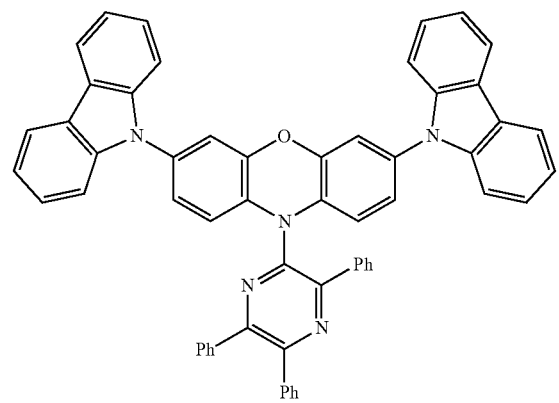
D-34
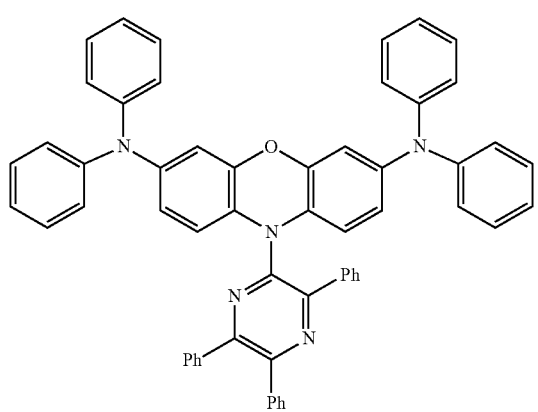
D-35
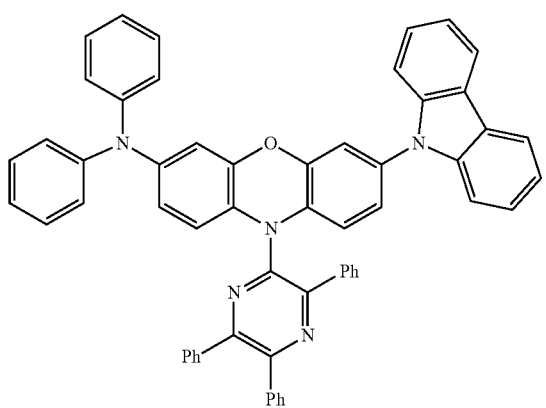
D-36
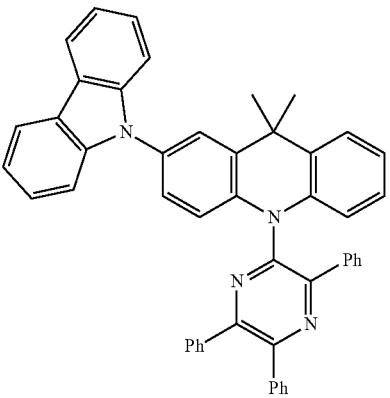
D-37
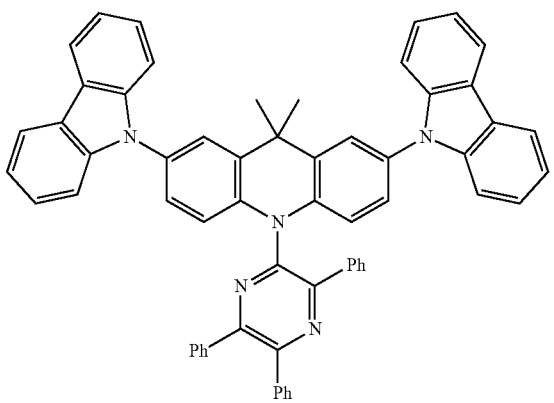
D-38
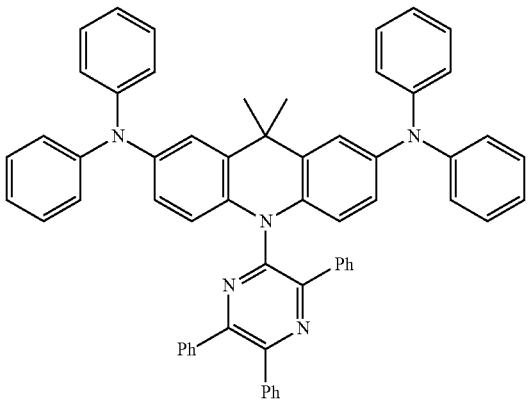
D-39

D-40
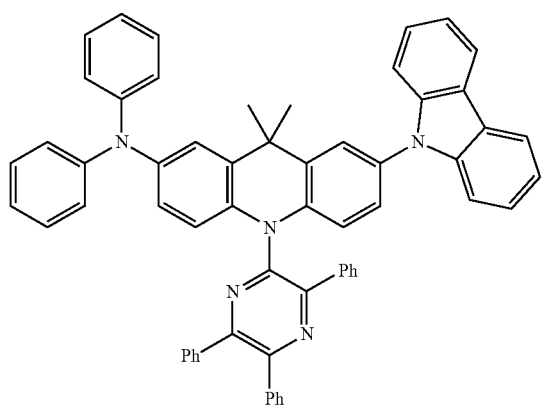
D-51
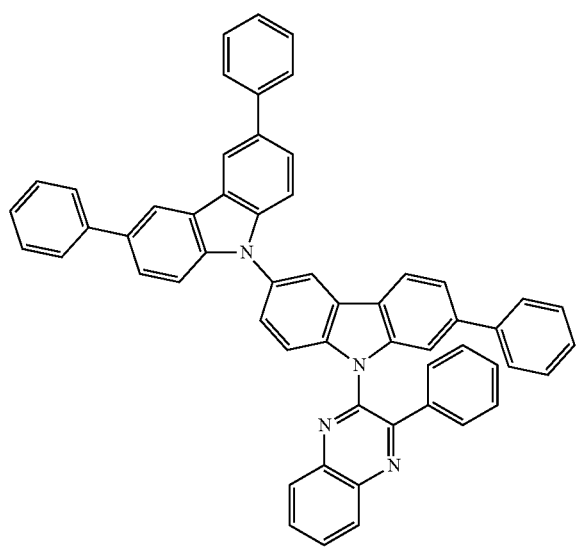
D-71
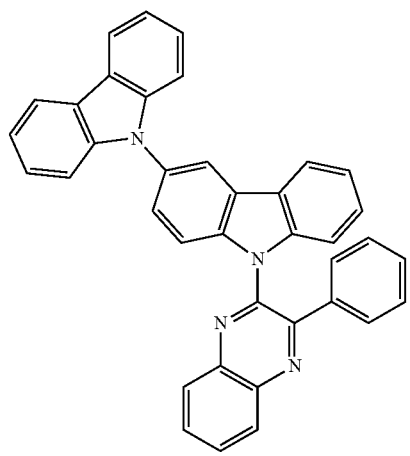
D-72
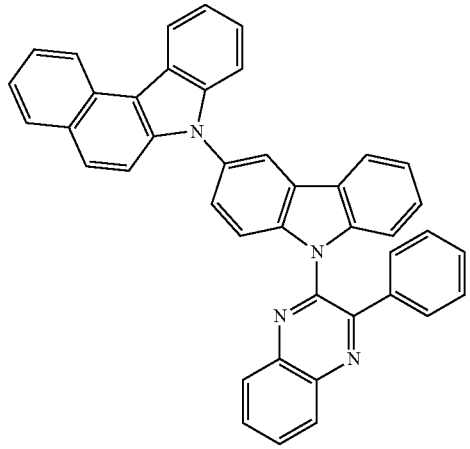
D-73
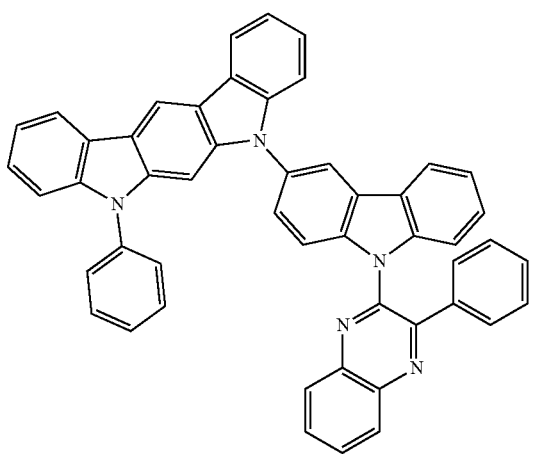
D-74
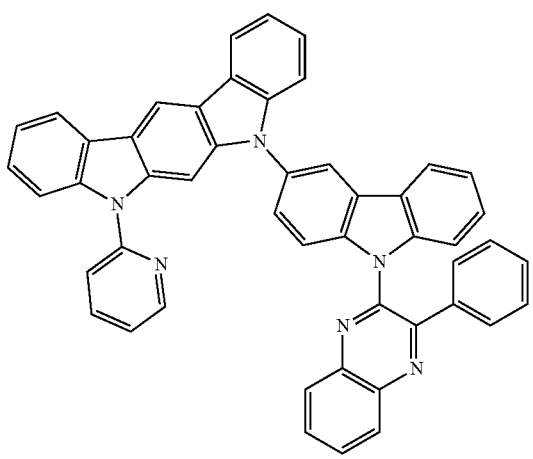

D-75
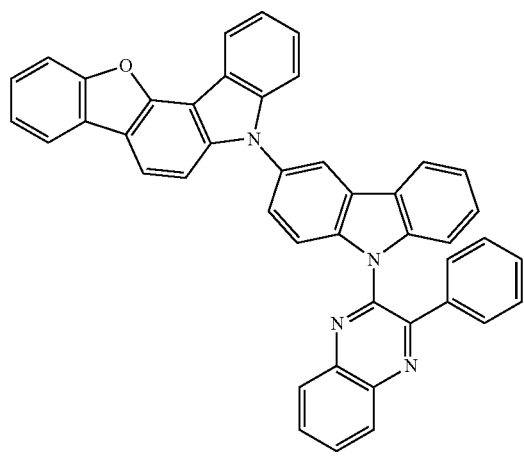
D-76
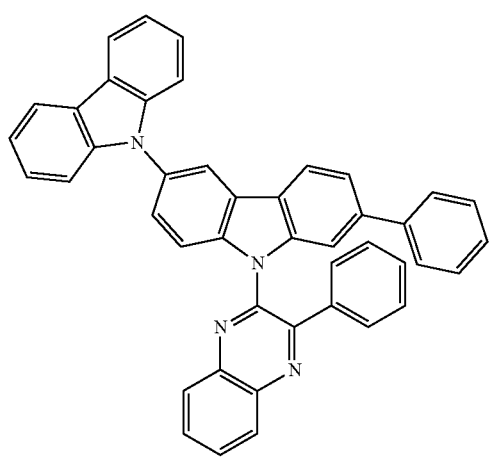
D-77
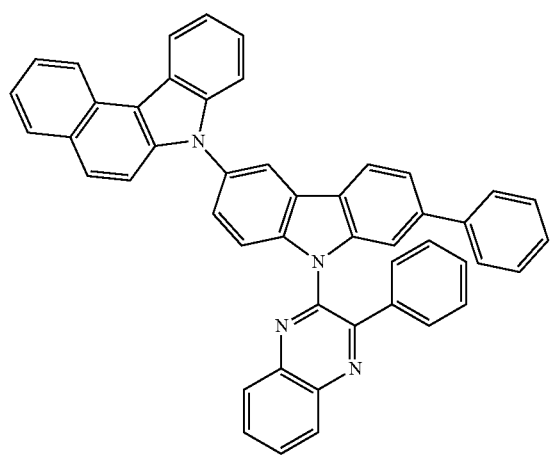
D-78
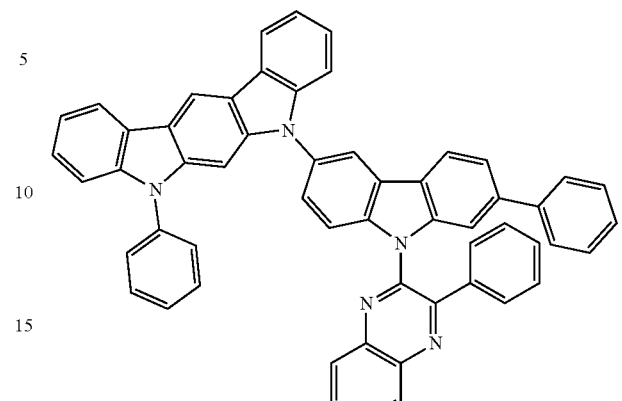
D-79
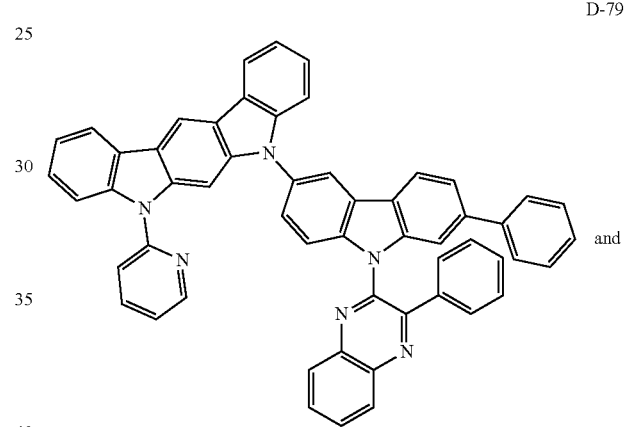
and
D-80
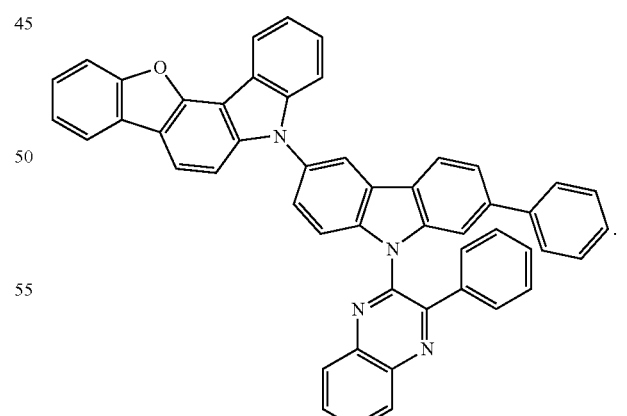
.
4. The organic electroluminescent device according to claim 1, wherein the compound represented by formula 8 is represented by the following formula 9:

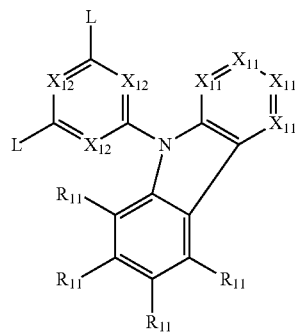

(9)

wherein $X_{11}$ independently represents N or $CR_{11}$;

$X_{12}$ independently represents N or $CR_{12}$;

$R_{11}$ and $R_{12}$ each independently represent hydrogen, deuterium, a substituted or unsubstituted (C1-C30)alkyl, a substituted or unsubstituted (C2-C30)alkenyl, a substituted or unsubstituted (C5-C30)aryl, a substituted or unsubstituted 5- to 30-membered heteroaryl, or CN; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$; and L independently represents hydrogen, a substituted or unsubstituted (C5-C30)aryl, or a substituted or unsubstituted 5- to 30-membered heteroaryl; or may be linked to an adjacent substituent to form a substituted or unsubstituted mono- or polycyclic, (C5-C30) alicyclic or aromatic ring, whose carbon atom(s) may be replaced with at least one heteroatom selected from nitrogen, oxygen, sulfur, Si, PO, SO, $SO_2$, and $SeO_2$.

5. The organic electroluminescent device according to claim 4, wherein $X_{12}$ independently represents N or CH.

6. The organic electroluminescent device according to claim 1, wherein the compound represented by formula 8 is selected from the group consisting of:

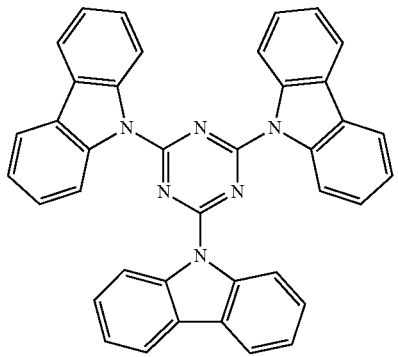
H-1

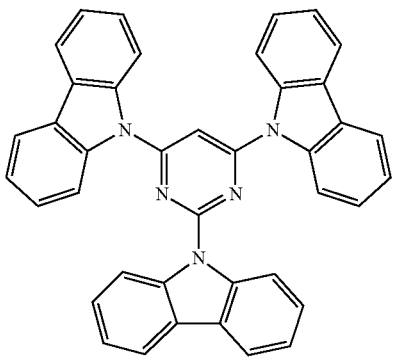
H-2

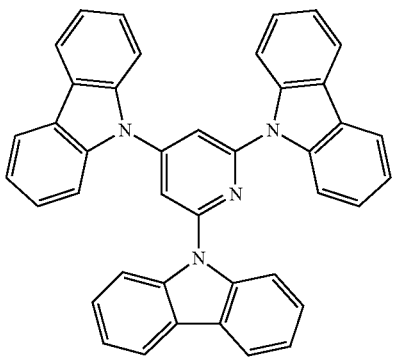
H-3

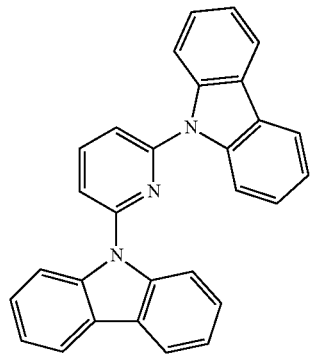
H-4

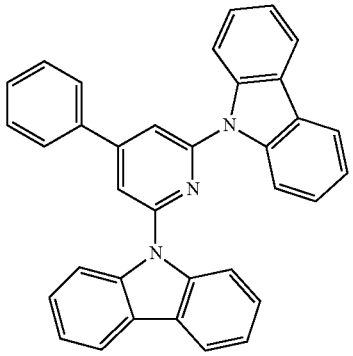
H-5

-continued
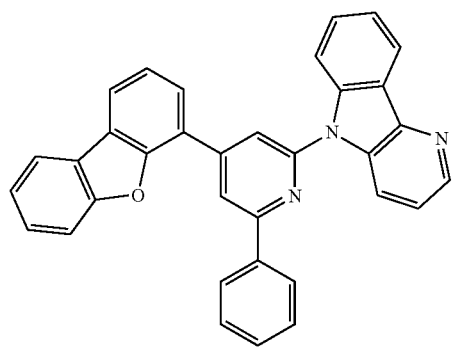
H-6
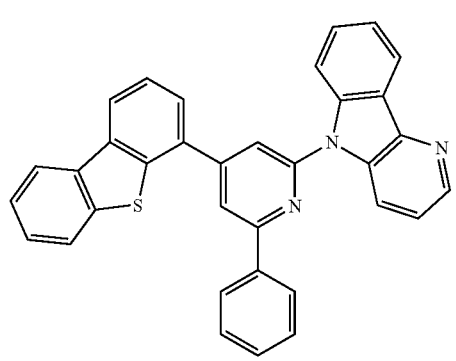
H-7
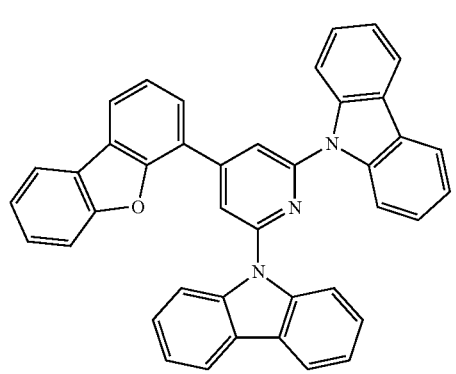
H-8
H-9
-continued
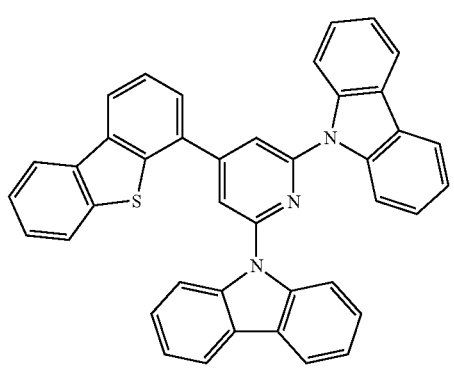
H-10
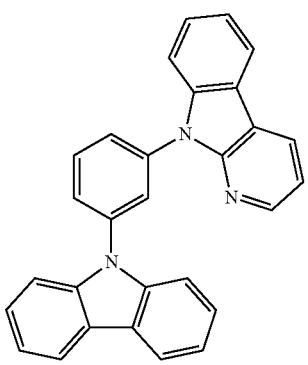
H-11
H-12
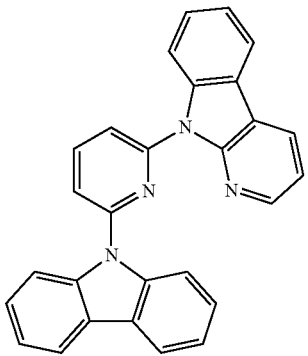
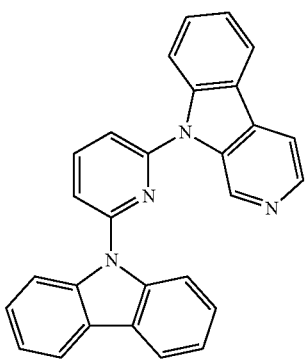
H-13

H-14 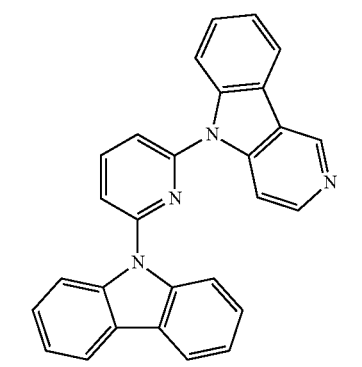
H-15 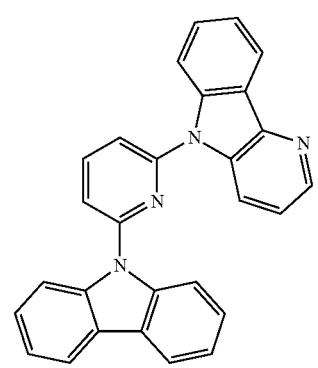
H-16 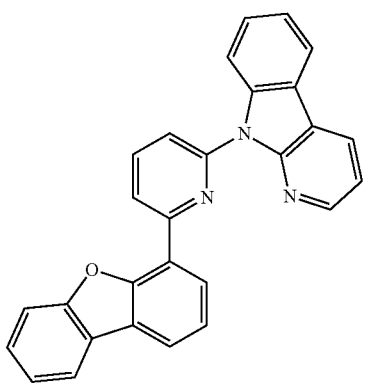
H-17 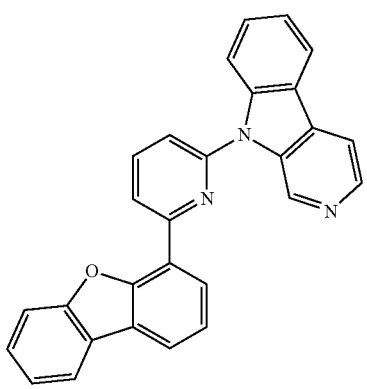
H-18 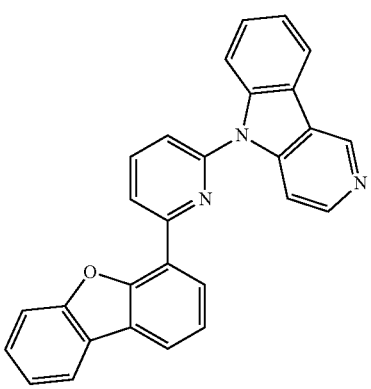
H-19 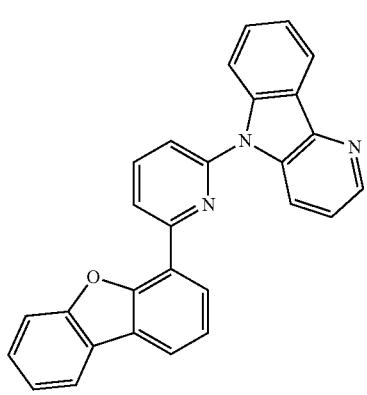
H-20 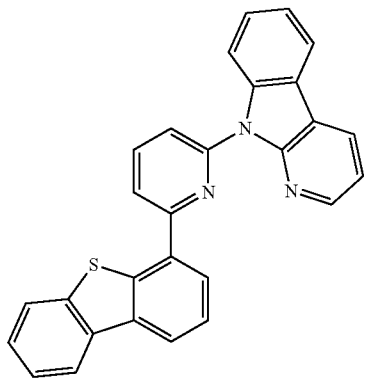
H-21 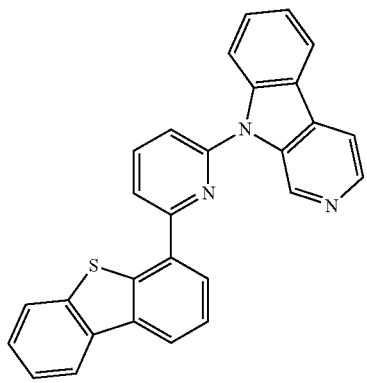

-continued
H-22
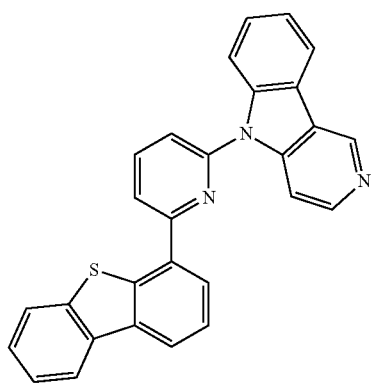
H-23
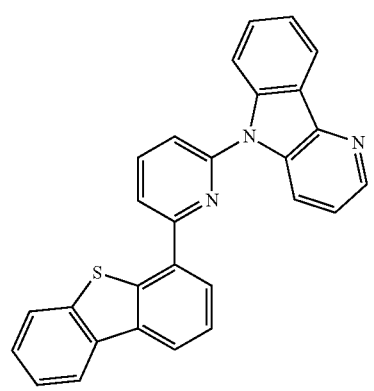
H-24
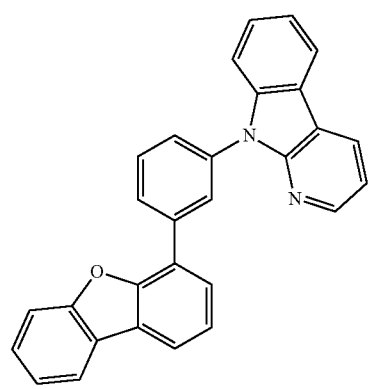
-continued
H-25
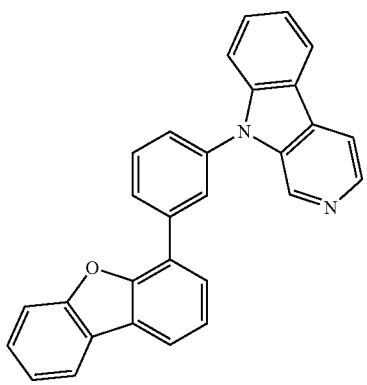
H-26
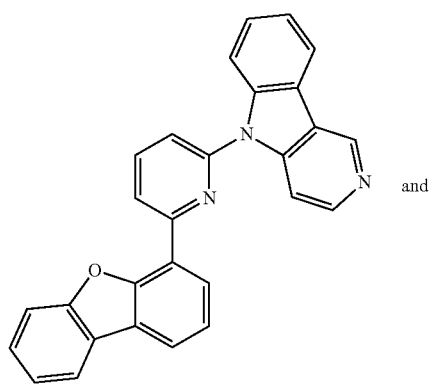
and
H-27
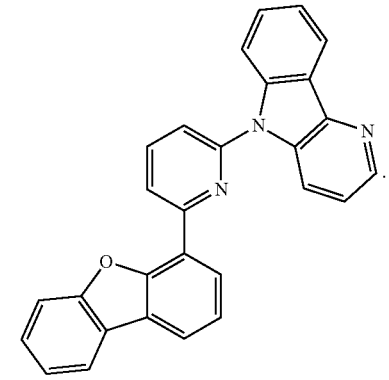
* * * * *